United States Patent
Parsons, IV et al.

(10) Patent No.: US 11,541,629 B2
(45) Date of Patent: Jan. 3, 2023

(54) MULTILAYERED NONWOVEN FABRICS AND METHOD OF MAKING THE SAME

(71) Applicants: PFNONWOVENS LLC, Hazleton, PA (US); PFNONWOVENS HOLDING S.R.O, Prague (CZ)

(72) Inventors: John Charles Parsons, IV, Dallas, PA (US); Peter Zajaczkowski, Greenville, SC (US); Karthik Ramaratnam, Dallas, PA (US); Sven Krister Mikael Erlandsson, Advance, NC (US); Pavlina Kasparkova, Znojmo (CZ)

(73) Assignees: PFNONWOVENS LLC, Hazleton, PA (US); PFNONWOVENS HOLDING S.R.O, Prague (CZ)

(*) Notice: Subject to any disclaimer, the term of this patent is extended or adjusted under 35 U.S.C. 154(b) by 635 days.

(21) Appl. No.: 16/415,258

(22) Filed: May 17, 2019

(65) Prior Publication Data

US 2019/0351648 A1    Nov. 21, 2019

Related U.S. Application Data

(60) Provisional application No. 62/672,933, filed on May 17, 2018.

(51) Int. Cl.
*B32B 5/26* (2006.01)
*B32B 5/02* (2006.01)
(Continued)

(52) U.S. Cl.
CPC ........ *B32B 5/26* (2013.01); *B32B 5/022* (2013.01); *D04H 1/43838* (2020.05); *D04H 1/56* (2013.01); *D04H 1/43825* (2020.05)

(58) Field of Classification Search
USPC ..... 428/212, 219, 317.1; 442/351, 327, 328; 156/161, 181, 209
See application file for complete search history.

(56) References Cited

U.S. PATENT DOCUMENTS

| 4,904,521 A | 2/1990 | Johnson et al. |
| 9,498,932 B2 * | 11/2016 | Richeson .............. B32B 5/08 |
| 2017/0246832 A1 * | 8/2017 | Moody, III .............. D01F 1/10 |

FOREIGN PATENT DOCUMENTS

| CN | 106076000 B | 5/2018 |
| WO | 0243951 A2 | 6/2002 |

(Continued)

OTHER PUBLICATIONS

Communication European Search Report completed on Jan. 20, 2022 in connection with European Patent Application No. 19804417.4.

*Primary Examiner* — Lynda Salvatore
(74) *Attorney, Agent, or Firm* — Amster, Rothstein & Ebenstein LLP

(57) ABSTRACT

A nonwoven composite fabric including a first nonwoven layer composed substantially of meltblown fibers, the fibers within the first nonwoven layer having diameters that vary in accordance with a first distribution, a second nonwoven layer composed substantially of meltblown fibers, the fibers within the second nonwoven layer having diameters that vary in accordance with a second distribution, and a third nonwoven layer composed substantially of meltblown fibers, the third nonwoven layer disposed between the first and second nonwoven layers, the fibers within the third nonwoven layer having diameters that vary in accordance with a third distribution that is greater than the first and second distributions.

20 Claims, 16 Drawing Sheets

(51) Int. Cl.
*D04H 1/56* (2006.01)
*D04H 1/4382* (2012.01)

(56) References Cited

FOREIGN PATENT DOCUMENTS

| | | | |
|---|---|---|---|
| WO | 2011041575 | A1 | 4/2011 |
| WO | 2011100407 | A1 | 8/2011 |
| WO | 2016206659 | A1 | 12/2016 |

* cited by examiner

| Process Parameter | Range | Exemplary Values |
|---|---|---|
| Meltblown Die, holes/inch | 35 - 75 | 35 |
| Meltblown Capillary Diameter, mm | 0.3 - 0.4 | 0.4 and 0.3 |
| Meltblown Die Temperature, °C | 250 - 280 | 255 |
| Meltblown Polymer Throughput Rate, kg/hr/m | 20 - 60 | 30 / 50 |
| Meltblown Hot Air Temperature, °C | 260 - 280 | 265 |
| Meltblown Hot Air Flow Rate, m$^3$/h | 2600 - 4000 | 2600/3900 |
| Meltblown Secondary Air Cooling Temperature, °C | 20 - 30 | 20, 30 |

FIG. 3

| Trial # | BW, gsm | # of MB Beams | gsm MB | %MB | MB resin | MB Profile | LSTS Average, seconds | AP, m³/min/m² |
|---|---|---|---|---|---|---|---|---|
| 1 | 13 | 3 | 2.0 | 16 | Resin A | flat | 7 | 95 |
| 2 | 13 | 3 | 2.0 | 16 | Resin A | flat | 8 | 83 |
| 3 | 13 | 3 | 2.5 | 19 | Resin A | flat | 8 | 73 |
| 4 | 13 | 3 | 2.5 | 19 | Resin B | hump | 14 | 50 |
| 5 | 15 | 3 | 2.8 | 19 | Resin B | basin | 16 | 37 |
| 6 | 17 | 3 | 3.2 | 19 | Resin B | hump | 23 | 33 |
| 7 | 19 | 3 | 3.6 | 19 | Resin B | hump | 33 | 32 |
| 8 | 15 | 3 | 2.8 | 19 | Resin B | hump | 22 | 37 |
| 9 | 17 | 3 | 3.2 | 19 | Resin B | hump | 29 | 30 |
| 10 | 19 | 3 | 3.6 | 19 | Resin B | hump | 35 | 29 |
| 11 | 13 | 3 | 2.5 | 19 | Resin B | hump | 15 | 50 |
| 12 | 15 | 3 | 3.0 | 20 | Resin C | flat | 20 | 32 |
| 13 | 15 | 3 | 3.0 | 20 | Resin C | gradient | 13 | 33 |
| 14 | 19 | 3 | 3.4 | 18 | Resin C | hump | 25 | 27 |
| 15 | 19 | 3 | 3.4 | 18 | Resin C | hump | 24 | 27 |
| 16 | 17 | 3 | 3.1 | 18 | Resin C | hump | 20 | 30 |
| 17 | 17 | 3 | 3.2 | 19 | Resin B | hump | 23 | 29 |
| 18 | 19 | 3 | 3.6 | 19 | Resin B | hump | 30 | 22 |
| 19 | 19 | 4 | 4.5 | 24 | Resin B | hump | 34 | 22 |
| 20 | 19 | 4 | 4.5 | 24 | Resin B | modified hump | 24 | 22 |
| 21 | 19 | 4 | 3.7 | 19 | Resin B | hump | 20 | 27 |
| 22 | 19 | 4 | 5.6 | 30 | Resin B | hump | 33 | 20 |
| 23 | 19 | 4 | 5.6 | 30 | Resin B | hump | 28 | 20 |
| 24 | 17 | 4 | 5.0 | 30 | Resin B | hump | 30 | 22 |
| 25 | 19 | 3 | 3.6 | 18 | Resin B | flat | 24 | 26 |
| 26 | 15 | 4 | 4.8 | 26 | Resin B | flat | 32 | 17 |
| 27 | 19 | 4 | 6.3 | 33 | Resin B | flat | 28 | 18 |
| 28 | 19 | 4 | 4.6 | 22 | Resin B | hump | 33 | 20 |
| 29 | 19 | 4 | 5.1 | 24 | Resin B | flat | 29 | 27 |
| 30 | 19 | 4 | 4.6 | 24 | Resin B | hump | 37 | 28 |
| 31 | 17 | 4 | 5.2 | 27 | Resin B | hump | 26 | 32 |
| 32 | 19 | 4 | 5.1 | 27 | Resin B | hump | 30 | 24 |
| 33 | 17 | 4 | 4.6 | 27 | Resin B | hump | 24 | 26 |
| 34 | 15 | 3 | 4.0 | 27 | Resin B | hump | 14 | 26 |
| 35 | 15 | 4 | 4.0 | 27 | Resin B | hump | 18 | 38 |
| 36 | 15 | 4 | 4.6 | 31 | Resin B | hump | 19 | 33 |
| 37 | 15 | 4 | 3.7 | 25 | Resin B | hump | 17 | 33 |
| 38 | 15 | 4 | 3.2 | 21 | Resin B | hump | 17 | 37 |
| 39 | 19 | 4 | 5.6 | 30 | Resin B | hump | 27 | 29 |
| 40 | 19 | 4 | 5.6 | 30 | Resin B | hump | 31 | 27 |
| 41 | 19 | 4 | 5.6 | 30 | Resin B | flat | 20 | 37 |
| 42 | 19 | 4 | 5.6 | 30 | Resin C | hump | 26 | 32 |
| 43 | 17 | 4 | 5.2 | 31 | Resin B | hump | 22 | 24 |
| 44 | 17 | 4 | 5.3 | 31 | Resin B | hump | 22 | 28 |
| 45 | 17 | 4 | 4.7 | 27 | Resin B | hump | 20 | 30 |
| 46 | 13 | 4 | 2.9 | 23 | Resin B | hump | 14 | 36 |
| 47 | 19 | 4 | 5.6 | 30 | Resin B | hump | 28 | 21 |

FIG. 4A

| Trial # | BW, gsm | # of MB Beams | gsm MB | distribution profile | distribution in layers | MB fiberProfile | MB Resin2 | note | LSTS Average, seconds | Air permeability Average, m3m2min |
|---|---|---|---|---|---|---|---|---|---|---|
| 1 | 13 | 3 | 2 | D-Flat | BBB | flat | A | | 7.00 | 95.00 |
| 2 | 13 | 3 | 2 | D-Flat | BBB | flat | A | | 8.00 | 85.00 |
| 3 | 13 | 3 | 2.5 | D-Flat | BBB | flat | A | | 8.00 | 73.00 |
| 4 | 13 | 3 | 2.5 | D-Hump | MBM | hump | B | | 14.00 | 50.00 |
| 5 | 15 | 3 | 2.8 | D-Hump | MBM | hump | B | | 16.00 | 37.30 |
| 6 | 17 | 3 | 3.2 | D-Hump | NMN | hump | B | | 23.00 | 31.00 |
| 7 | 19 | 3 | 3.6 | D-Flat | NNN | hump | B | | 23.00 | 31.70 |
| 8 | 15 | 3 | 2.8 | D-Hump | NBN | hump | B | 2 | 21.50 | 37.20 |
| 9 | 17 | 3 | 3.2 | D-Hump | NMN | hump | B | 2 | 28.90 | 29.80 |
| 10 | 19 | 3 | 3.6 | D-Hump | NMN | hump | B | 2 | 34.60 | 28.70 |
| 11 | 13 | 3 | 2.5 | D-Hump | MBM | hump | B | | 15.00 | 50.00 |
| 12 | 19 | 3 | 3.9 | D-Flat | NNN | flat | C | | 20.00 | 32.00 |
| 13 | 19 | 3 | 3.9 | D-Gradient | NMB | gradient | C | | 13.00 | 33.00 |
| 14 | 19 | 3 | 3.4 | D-Hump | MBM | hump | C | | 25.00 | 27.00 |
| 15 | 19 | 3 | 3.4 | D-Hump | MBM | hump | C | | 24.00 | 27.00 |
| 16 | 17 | 3 | 3.1 | D-Hump | MBM | hump | C | | 20.00 | 30.00 |
| 17 | 17 | 3 | 3.2 | D-Hump | MBM | hump | B | | 21.00 | 29.00 |
| 18 | 19 | 4 | 5.6 | D-Hump | NMMN | hump | B | | 30.00 | 22.00 |
| 19 | 19 | 4 | 4.5 | D-Hump | NMMN | hump | B | | 24.00 | 22.00 |
| 20 | 19 | 4 | 4.5 | D-Hump | NMMN | modified hump | B | 1 | 24.00 | 22.00 |
| 21 | 19 | 4 | 3.7 | D-Hump | NMMN | hump | B | | 20.00 | 22.00 |
| 22 | 19 | 4 | 5.6 | D-Hump | NMMN | hump | B | | 33.00 | 20.00 |
| 23 | 19 | 4 | 5.6 | D-Hump | NMMN | hump | B | 1 | 28.00 | 20.00 |
| 24 | 17 | 4 | 5 | D-Hump | NMMN | hump | B | 1 | 22.00 | 22.00 |
| 25 | 19 | 4 | 3.6 | D-Hump | NMMN | flat | B | | 30.00 | 17.00 |
| 26 | 19 | 4 | 4.8 | D-Hump | NMMN | flat | B | | 32.00 | 18.00 |

FIG. 4B

| Trial # | BW, gsm | # of MB Beams | gsm MB | distribution profile | distribution in layers | MB fiberProfile | MB Resin2 | note | LSTS Average, seconds | Air permeability Average, m3m2min |
|---|---|---|---|---|---|---|---|---|---|---|
| 27 | 19 | 4 | 6.3 | D-Hump | NMMN | flat | B | | 28.00 | 20.00 |
| 28 | 19 | 4 | 5.1 | D-Flat | NNNN | hump | B | 2 | 33.00 | 27.00 |
| 29 | 19 | 4 | 4.6 | D-Hump | NMMN | flat | B | | 29.00 | 21.00 |
| 30 | 19 | 4 | 5.4 | D-Flat | MMMM | hump | B | | 27.00 | 28.00 |
| 31 | 17 | 4 | 4.6 | D-Flat | MMMM | hump | B | | 26.00 | 32.00 |
| 32 | 19 | 4 | 5.1 | D-Hump | NMMN | hump | B | | 30.00 | 24.00 |
| 33 | 17 | 4 | 4.6 | D-Flat | NNNN | hump | B | | 24.00 | 26.00 |
| 34 | 15 | 4 | 4 | D-Flat | BBBB | hump | B | | 14.11 | 45.52 |
| 35 | 15 | 4 | 4 | D-Flat | BBBB | hump | B | | 18.45 | 37.76 |
| 36 | 15 | 4 | 4.6 | D-Flat | BBBB | hump | B | | 19.17 | 32.56 |
| 37 | 15 | 4 | 3.7 | D-Flat | BBBB | hump | B | | 17.42 | 33.29 |
| 38 | 15 | 4 | 3.2 | D-Hump | MBBM | hump | B | | 17.13 | 36.62 |
| 39 | 19 | 4 | 5.6 | D-Flat | NNNN | hump | B | | 27.00 | 29.00 |
| 40 | 19 | 4 | 5.6 | D-Flat | MMMM | hump | B | | 31.00 | 27.00 |
| 41 | 19 | 4 | 5.6 | D-Flat | BBBB | hump | C | | 20.00 | 37.00 |
| 42 | 19 | 4 | 5.6 | D-Flat | MMMM | hump | B | | | |
| 43 | 17 | 4 | 5.3 | D-Hump | NMMN | hump | B | | 26.00 | 23.00 |
| 44 | 17 | 4 | 5.3 | D-Flat | MMMM | hump | B | | 22.00 | 27.00 |
| 45 | 15 | 4 | 4.7 | D-Flat | MMMM | hump | B | | 20.00 | 30.00 |
| 46 | 13 | 4 | 2.9 | D-Hump | MBBM | hump | B | | 14.00 | 39.00 |
| 47 | 19 | 4 | 5.6 | D-Hump | NMMN | hump | B | | 28.30 | 21.30 |
| 50 | 10 | 3 | 1.4 | D-Hump | NMN | hump | A | | 10.00 | 58.00 |
| 51 | 13 | 3 | 6 | D-Hump | NMN | flat | C | | 87.00 | 27.00 |
| 52 | 26 | 2x3 | 12 | D-Hump | NMN-NMN | flat | C | | over 100 | 13.00 |

1) nonwoven damaged during calandering. Certain level of burnouts affects LSTS but does not affect the Air Permeability value.

2) spunbond fibers from composition with lower surface tension composition than other samples.

FIG. 4B (continued)

MULTILAYERED NONWOVEN FABRICS AND METHOD OF MAKING THE SAME

RELATED APPLICATIONS

This application claims priority to and the benefit of U.S. Provisional Application No. 62/672,933, entitled MULTILAYERED NONWOVEN FABRICS AND METHOD OF MAKING THE SAME and filed May 17, 2018, the contents of which are incorporated herein by reference in their entirety.

FIELD OF THE INVENTION

The present invention relates to multilayered nonwovens and an improved method of manufacturing multilayered nonwovens.

BACKGROUND OF THE INVENTION

Continued improvements in nonwoven fabrics is of interest in personal care products (e.g. baby diapers, feminine care, adult products) and medical care barrier products (e.g. gowns, chucks, drapes, aprons, and the like) both for functional and perceptual reasons. In particular, abrasion and water resistance, as well as softness, of a fabric are properties that are of interest. Additionally, water resistant fabrics with improved leakage protection—in other words, with improved surface dryness—are desirable.

SUMMARY OF THE INVENTION

The present invention is directed to an improved multilayered nonwoven fabric that may be used, for example, with disposable absorbent articles, such as disposable diapers, incontinence and feminine care products, and disposable products for the medical and other industries. Specifically, in a nonwoven laminate having outer spunbond layers and an inner meltblown layer (SMS), the inner meltblown layer may be made up of three or more sublayers, with at least two outer fine fiber layers (fiber diameter at or below 2 microns) and one or more inner coarse fiber layers (fiber diameter above 2 microns).

In an exemplary embodiment, a nonwoven composite fabric comprises at least first and second nonwoven webs composed substantially of spunbond fibers; and a third nonwoven web composed substantially of meltblown fibers disposed between the first and second nonwoven webs and bonded to the first and second nonwoven webs, the third nonwoven web comprising one or more inner coarse fiber layers disposed between two or more outer fine fiber layers.

In at least one embodiment, the third nonwoven web is thermally bonded to the first and second nonwoven webs.

In an exemplary embodiment, the nonwoven composite fabric has a high degree of fluid barrier characteristics and maintains surface dryness and softness.

In an exemplary embodiment, the one or more inner coarse fiber layers comprise meltblown fibers with diameters above 2 microns.

In an exemplary embodiment, the one or more inner coarse fiber layers have an average fiber diameter of greater than 2 microns.

In an exemplary embodiment, the two or more outer fine fiber layers comprise meltblown fibers with diameters at or below 2 microns.

In an exemplary embodiment, the two or more outer fine fiber layers have an average fiber diameter of less than 2 microns.

In an exemplary embodiment, a difference in average fiber diameter between the one or more inner coarse fiber layers and the two or more outer fine fiber layers is between 0.5 microns and 3 microns.

In an exemplary embodiment, the difference in average fiber diameter between the one or more inner coarse fiber layers and the two or more outer fine fiber layers is between 1 micron and 2.7 microns.

In an exemplary embodiment, the nonwoven composite fabric has an average Low Surface Tension Fluid Strikethrough Time of at least approximately 25 seconds and an air permeability below approximately 35 $m^3/min/m^3$.

In an exemplary embodiment, a nonwoven composite fabric comprises at least first and second nonwoven webs composed substantially of spunbond fibers; and a third nonwoven web composed substantially of meltblown fibers disposed between the first and second nonwoven webs and bonded to the first and second nonwoven webs, the third nonwoven web comprising one or more inner coarse fiber layers disposed between two or more outer fine fiber layers, and the third nonwoven web comprising at least two transition zones each having a size differential of between 0.5 microns and 3 microns.

In at least one embodiment, the third nonwoven web is thermally bonded to the first and second nonwoven webs.

In an exemplary embodiment, a nonwoven laminate comprises one or more first nonwoven web layers comprised substantially of coarse meltblown fibers, at least two second nonwoven web layers comprised substantially of fine meltblown fibers, and at least two third nonwoven web layers comprised substantially of spunbond fibers, wherein the nonwoven laminate comprises a bond pattern.

In at least one embodiment, the bond pattern is imparted by thermally bonding the web layers.

In an exemplary embodiment, a process of manufacturing a nonwoven laminate, comprises forming an inner web comprised substantially of meltblown fibers by depositing one or more coarse fiber sublayers between two or more fine fiber sublayers, bonding two or more outer webs comprised substantially of spunbond fibers to the inner web, wherein the laminate comprises about 10-40% meltblown fibers by weight.

In an exemplary embodiment, a nonwoven laminate comprises at least two first nonwoven webs; and a second nonwoven web bonded between the first nonwoven webs, wherein the first nonwoven webs each comprise one or more first layers of continuous fibers including a first polymer component, the continuous fibers of the first nonwoven webs having a first average diameter, and the second nonwoven web comprises one or more second layers of continuous fibers between at least two third layers of continuous fibers, the continuous fibers of the second nonwoven web having a second average diameter less than the first average diameter, and the continuous fibers of the third layers having a third average diameter less than a fourth average diameter of the continuous fibers of the second layers.

In at least one embodiment, the first polymer component is a polyolefin, such as polypropylene.

In at least one embodiment, the first polymer component is viscose.

In at least one embodiment, the continuous fibers of the first layer comprise a second polymer component.

In at least one embodiment, the second polymer component is a polyolefin, such as polypropylene.

In at least one embodiment, the continuous fibers of the first layer are blended or bicomponent fibers.

In at least one embodiment, the nonwoven laminate has a basis weight within the range of 5 gsm to 100 gsm.

In at least one embodiment, the nonwoven laminate has a basis weight within the range of 5 gsm to 80 gsm.

In at least one embodiment, the nonwoven laminate has a basis weight within the range of 5 gsm to 60 gsm.

In at least one embodiment, the nonwoven laminate has a basis weight within the range of 11 gsm to 19 gsm.

In at least one embodiment, meltblown fibers comprise between 2% and 45% of the total weight of the nonwoven laminate.

In at least one embodiment, meltblown fibers comprise between 16% and 33% of the total weight of the nonwoven laminate.

In at least one embodiment, the first nonwoven webs respectively form a top sheet and a back sheet of the nonwoven laminate.

According to an exemplary embodiment of the present invention, a method of making a nonwoven web comprises: forming a first nonwoven web comprising continuous spunbond fibers; forming a second nonwoven web comprising continuous meltblown fibers by forming one or more coarse fiber sublayers with coarse meltblown fibers between at least two fine fiber sublayers with fine meltblown fibers; forming a third nonwoven web comprising continuous spunbond fibers; and bonding the first, second, and third nonwoven webs to form respective first, second, and third layers.

In at least one embodiment, the step of forming the first nonwoven web comprises a spunmelt process.

In at least one embodiment, the step of forming the second nonwoven web comprises a meltblown process.

According to an exemplary embodiment of the present invention, a nonwoven composite fabric comprises at least first and second nonwoven webs composed substantially of spunbond fibers; and a third nonwoven web composed substantially of meltblown fibers disposed between the first and second nonwoven webs and bonded to the first and second nonwoven webs, wherein the third nonwoven web comprises two or more inner coarse fiber layers, each of the coarse fiber layers being disposed between two or more outer fine fiber layers, wherein the third nonwoven web comprises at least four transition zones having a size differential of between 0.5 microns and 3 microns.

According to an exemplary embodiment of the present invention, a nonwoven composite fabric comprises at least first and second nonwoven webs composed substantially of spunbond fibers; and a third nonwoven web composed substantially of meltblown fibers disposed between the first and second nonwoven webs and bonded to the first and second nonwoven webs, wherein the third nonwoven web comprises one or more inner coarse fiber layers, each of the coarse fiber layers being disposed between two or more outer fine fiber layers, wherein the third nonwoven web comprises at least three transition zones having a size differential of between 0.5 microns and 3 microns.

In at least one embodiment, the third nonwoven web is thermally bonded to the first and second nonwoven webs.

A nonwoven composite fabric according to an exemplary embodiment of the present invention comprises: a first nonwoven layer composed substantially of meltblown fibers, the fibers within the first nonwoven layer having diameters that vary in accordance with a first distribution; a second nonwoven layer composed substantially of meltblown fibers, the fibers within the second nonwoven layer having diameters that vary in accordance with a second distribution; and a third nonwoven layer composed substantially of meltblown fibers, the third nonwoven layer disposed between the first and second nonwoven layers, the fibers within the third nonwoven layer having diameters that vary in accordance with a third distribution that is greater than the first and second distributions.

In at least one exemplary embodiment, the first and second nonwoven layers make up at least 30 weight % of the first, second and third nonwoven layers combined.

In at least one exemplary embodiment, the first and second distributions are narrow or middle distributions, where narrow distribution indicates at least one increment of a sample of fibers forming a peak within the sample that has a frequency equal to or greater than 30% or indicates at least one increment of a sample of fibers forming a peak within the sample that has a frequency equal to or greater than 20% and no other peak over 5%, and where middle distribution indicates at least one increment of a sample of fibers forming a first peak within the sample that has a frequency equal to or greater than 20% and at least one other increment forming a second peak within the sample that has a frequency greater than 5%.

In at least one exemplary embodiment, the third distribution is a middle or broad distribution, where broad distribution indicates that no increment of a sample of fibers forms a peak within the sample that has a frequency equal to or greater than 20%.

In at least one exemplary embodiment, the first and second distributions are narrow distributions.

In at least one exemplary embodiment, the third distribution is a middle distribution.

In at least one exemplary embodiment, the third distribution is a broad distribution.

In at least one exemplary embodiment, the first and second distributions are middle distributions.

In at least one exemplary embodiment, the third distribution is a broad distribution.

In at least one exemplary embodiment, an increment coefficient between the first distribution and the third distribution and between the second distribution and third distribution is at least 1.

In at least one exemplary embodiment, the increment coefficient is at least 1.5.

In at least one exemplary embodiment, the nonwoven composite fabric further comprises at least one layer composed substantially of spunbond fibers.

In at least one exemplary embodiment, the first, second and third layers are disposed between at least two outer layers, the at least two outer layers composed substantially of spunbond fibers.

In at least one exemplary embodiment, the nonwoven composite fabric has a basis weight of less than 10 gsm.

In at least one exemplary embodiment, the nonwoven composite fabric has a Low Surface Tension Fluid Strike-through Time of at least 25 seconds.

In at least one exemplary embodiment, the nonwoven composite fabric has an air permeability of less than 50 $m^3/min/m^3$.

In at least one exemplary embodiment, the fibers in the first and second nonwoven layers have an average fiber diameter that is less than an average fiber diameter of the fibers in the third nonwoven layer.

In at least one exemplary embodiment, the fibers within the first, second and third nonwoven layers have an average diameter of less than 2 microns.

A nonwoven composite fabric according to an exemplary embodiment of the present invention comprises: a first web comprising: a first nonwoven layer composed substantially of meltblown fibers, the fibers within the first nonwoven layer having diameters that vary in accordance with a first distribution; a second nonwoven layer composed substantially of meltblown fibers, the fibers within the second nonwoven layer having diameters that vary in accordance with a second distribution; a third nonwoven layer composed substantially of meltblown fibers, the third nonwoven layer disposed between the first and second nonwoven layers, the fibers within the third nonwoven layer having diameters that vary in accordance with a third distribution that is greater than the first and second distributions; and a fourth nonwoven layer composed substantially of spunbond fibers; and a second web comprising: a fifth nonwoven layer composed substantially of meltblown fibers, the fibers within the fifth nonwoven layer having diameters that vary in accordance with a fifth distribution; a sixth nonwoven layer composed substantially of meltblown fibers, the fibers within the sixth nonwoven layer having diameters that vary in accordance with a sixth distribution; and a seventh nonwoven layer composed substantially of meltblown fibers, the seventh nonwoven layer disposed between the fifth and sixth nonwoven layers, the fibers within the seventh nonwoven layer having diameters that vary in accordance with a seventh distribution that is greater than the fifth and sixth distributions, the first and second webs are disposed adjacent to one another so that the second nonwoven layer is directly facing with the sixth nonwoven layer.

In at least one exemplary embodiment, the second web further comprises an eighth nonwoven layer composed substantially of spunbond fibers.

Other features and advantages of the present invention will become readily apparent from the following detailed description and the accompanying drawings.

BRIEF DESCRIPTION OF THE DRAWINGS

The above and related objects, features and advantages of the present invention will be more fully understood by reference to the following, detailed description of the preferred, albeit illustrative, embodiment of the present invention when taken in conjunction with the accompanying figures, wherein:

FIG. 3 is a table of selective processing parameters for the MB layers in accordance with exemplary embodiments of the present invention;

FIG. 4A is a table of selective results for nonwoven fabrics according to exemplary embodiments of the present invention;

FIG. 4B is a table of selective results for nonwoven fabrics according to exemplary embodiments of the present invention;

DETAILED DESCRIPTION

Figure 1:
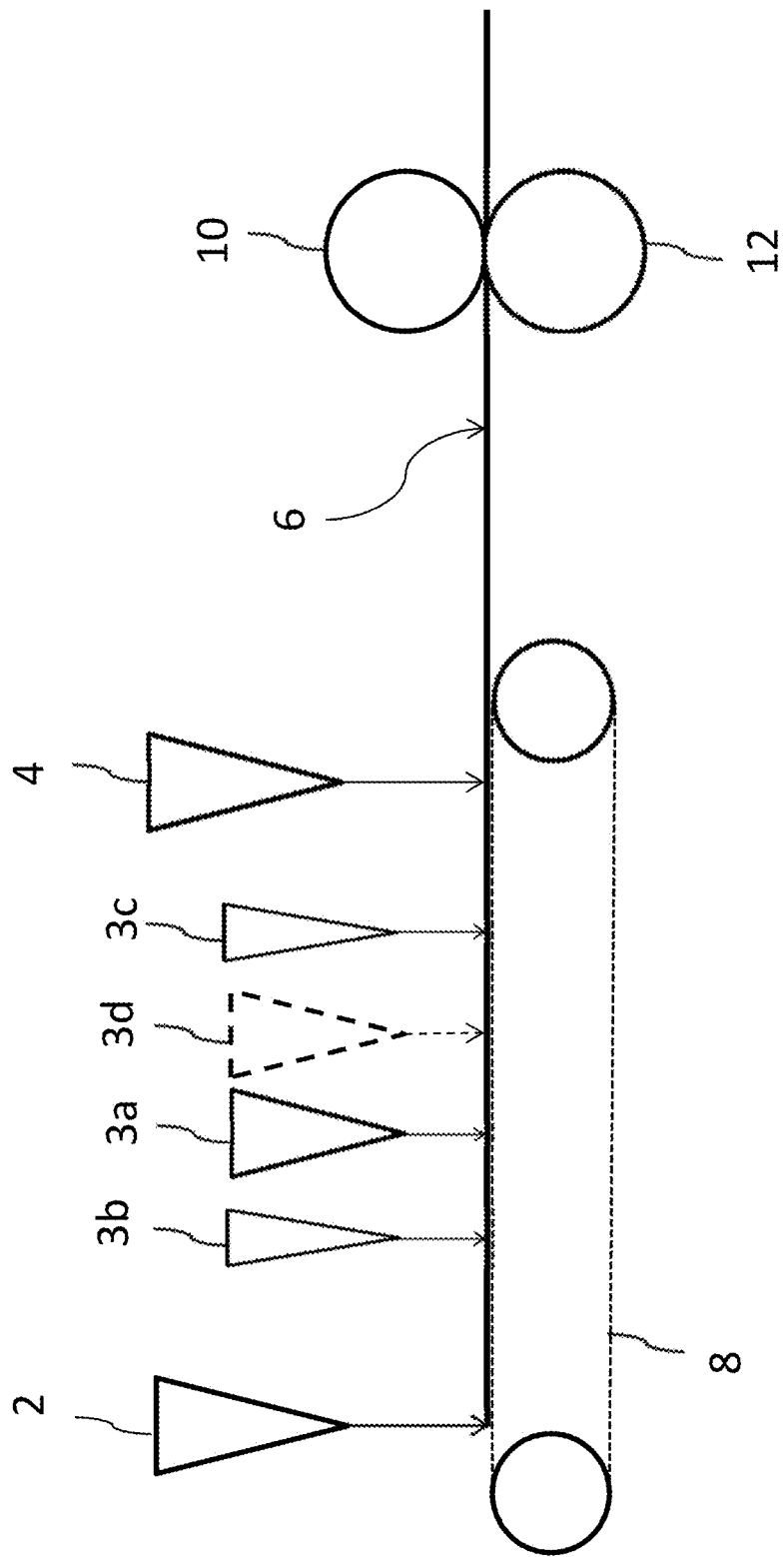
FIG. 1 is a representative diagram of a system for producing nonwoven fabrics comprising at least one inner coarse meltblown (MB) fiber layer between at least two outer fine MB fiber layers that are, in turn, disposed between at least two spunbond layers according to a first exemplary embodiment of the present invention.

The present invention is directed to nonwoven fabrics with improved barrier characteristics and surface dryness and methods for producing same.

For the purposes of the present disclosure, increments of a sample of fiber diameter measurements will be used to determine fiber distribution within a layer of a composite fabric, where each increment is 0.25 micron.

Also, for the purposes of the present disclosure, the term "air permeability" and "AP" are interchangeable.

A composite nonwoven web with at least one inner coarse meltblown (MB) fiber layer between at least two outer fine MB fiber layers, which are, in turn, disposed between at least two spunbond layers, in accordance with exemplary embodiments of the present invention is especially suitable for use in disposable absorbent articles and/or medical garments requiring a high liquid barrier. As used herein, the term "absorbent article" refers to articles which absorb and contain fluids and solid materials. For example, absorbent articles may be placed against or in proximity to the body to absorb and contain the various exudates discharged by the body. Absorbent articles may be articles that are worn, such as baby diapers, adult incontinence products, and feminine care products, or hygienic and barrier products that are used to absorb and contain fluids and solid materials, such as disposable gowns and chucks as used in the medical profession. In particular, the nonwovens may be used as or as part of a body contacting layer such as a topsheet, leg cuff, or back-sheet. The nonwovens may also be used for packaging or wrapping items such as absorbent articles. The term "disposable" is used herein to describe absorbent articles which are not intended to be laundered or otherwise restored or reused as an absorbent article, but instead are intended to be discarded after a single use and, preferably, to be recycled, composted or otherwise disposed of in an environmentally compatible manner.

The terms "nonwoven fabric, sheet, layer or web" as used herein means a structure of individual fibers, filaments, or threads that are positioned in a substantially random manner to form a planar material, as opposed to a knitted or woven fabric. Examples of nonwoven fabrics include meltblown webs, spunbond webs, carded webs, air-laid webs, wet-laid webs, and spunlaced webs. A nonwoven composite fabric comprises more than one nonwoven layer.

The term "spunbond fibers" as used herein means substantially continuous fibers or filaments having an average diameter in the range of 5-30 microns. Splittable bicomponent or multicomponent fibers having an average diameter in the range of 10-30 microns prior to splitting are also included.

The term "meltblown fibers" as used herein, means substantially continuous fibers or filaments having an average diameter of less than 10 microns.

An exemplary embodiment of the present invention may include changing the MB and/or SB fiber diameter to further improve the tactile feel of the material without detracting from abrasion performance.

An exemplary embodiment of the present invention includes a multi-layer composite fabric comprising at least one first layer of fibers (preferably meltblown) that comprises three or more sublayers of varying fiber diameters bonded to at least one second layer of fibers (preferably spunbond) where the median fiber diameter of the second layer of fibers is at least 1.3 times greater than the median fiber diameter of the first layer. An exemplary nonwoven fabric can be formed in-line by sequentially depositing one or more layers of spunbond fibers, followed by three or more layers of meltblown fibers, and further followed by another one or more layers of spunbond fibers on a moving collecting surface. The assembled layers can be thermally bonded by passing them through a calender nip formed between two calender rolls. Each calender roll may be heated or it may be unheated. Each calender roll may have a pattern or it may be smooth. Alternatively, the layers may be bonded ultrasonically, chemically (for example, with adhesives), or through air bonding. In an alternative embodiment, the individual layers can be pre-formed and optionally bonded and collected individually such as by winding the fabrics on wind-up rolls. The individual layers can then be assembled by layering at a later time and bonded together to form a composite fabric.

In embodiments, the base fabric may be an "SMS" structure that may be produced with multiple beams of both spunbond and meltblown wherein the fabric has outer spunbond layers and inner meltblown layers of varying fiber diameters. According to an embodiment of the invention, the base fabric is thermally pattern bonded.

A process for making a composite fabric according to an exemplary embodiment of the present invention is shown in FIG. 1. First, spunbond beam 2, meltblown beams 3a-3d and spunbond beam 4 are used to form a nonwoven web (hereinafter also referred to as "fabric" or "base fabric") 6 on conveyor belt 8. The web 6 is then bonded with calender rolls 10 and 12. According to an exemplary embodiment of the invention, plural meltblown fiber sublayers may be formed using respective beams 3a, 3b, 3c, and optionally, 3d. Beam 3a may be a meltblown beam for depositing "coarse" fibers with diameters above 2 microns while beams 3b and 3c respectively deposit "fine" fibers with diameters equal to or below 2 microns. Accordingly, beams 3a, 3b, and 3c may collectively form a meltblown web comprising at least three sublayers, wherein a "coarse" fiber sublayer is formed between two "fine" fiber sublayers. As further illustrated in FIG. 1, an additional "coarse" fiber beam 3d may be incorporated to form another "coarse" fiber sublayer within the two "fine" fiber sublayers formed by beams 3b and 3c. The diameters of the fibers deposited by beams 3a and 3d may be the same or different. In accordance with additional embodiments of the invention, plural elements corresponding to each of beams 2 and 4 may also be incorporated in the system to form multiple respective layers of web 6.

According to an exemplary embodiment of the invention, a spunmelt nonwoven web is made of substantially continuous filaments that are laid down on a moving conveyor belt 8 in a randomized distribution. Resin pellets may be processed under heat into a melt and then fed through a spinneret (or spinning beams 2 and 4) to create hundreds of filaments by use of a drawing device (not shown). As described before, multiple spinnerets or beams (blocks in tandem) may be used to provide an increased density of spunbond fibers corresponding to, for example, each of spinning beams 2 and 4. Jets of a fluid (such as air) cause the fibers from beams 2 and 4 to be elongated, and the fibers are then blown or carried onto a moving web (conveyor belt) 8 where they are laid down and sucked against the web 8 by suction boxes (not shown) in a random pattern to create a fabric structure 6. A meltblown layer, with at least three sublayers, may be deposited by meltblown mechanisms (or "beams") 3a-3d between spunbond layers laid by spinning beams 2 and 4. For example, the meltblowing process includes inserting a thermoplastic polymer into a die. The thermoplastic polymer material is extruded through a plurality of fine capillaries in the die to form fibers. The fibers stream into a high velocity gas (e.g. air) stream which attenuates the streams of molten thermoplastic polymer material to reduce their diameter, which may be to the microfiber diameter. The meltblown fibers are quasi-randomly deposited by beams 3a-3d over the spunbond layer laid by spinning beam 2 to form a meltblown web. Multiple dies are placed side by side in a block to generate sufficient fibers across the total width of the nonwoven fabric 6, and two or more blocks may be used in tandem in order to increase the coverage of fibers. The meltblown fibers can be tacky when they are deposited, which generally results in some bonding between the meltblown fibers of the web.

In a preferred embodiment, the fibers used to form web 6 are thermoplastic polymers, examples of which include polyolefins, polyesters (e.g., polylactic acid or "PLA"), polyamides, copolymers thereof (with olefins, esters, amides or other monomers) and blends thereof. As used herein, the term "blend" includes either a homogeneous mixture of at least two polymers or a non-homogeneous mixture of at least two physically distinct polymers such as bicomponent fibers. Preferably the fibers are made from polyolefins, examples of which include polyethylene, polypropylene, propylene-butylene copolymers thereof and blends thereof, including, for example, ethylene/propylene copolymers and polyethylene/polypropylene blends. In an exemplary embodiment, the spunbond fibers include additives to improve softness. Examples of such additives include copolymers; slip additives; and other soft additives. Additives, such as those described above and the like, may also be added to the MB fibers in order to modify surface feel and physical performance e.g. absorption rate.

In an exemplary embodiment, web 6 may be thermally calender bonded via rollers 10 and 12. In addition, a degree of bonding may be imparted by the meltblown fibers (from beams 3a-3d) as a result of low pressure calendering or during the initial web formation due to the meltblown fibers staying at a sufficiently high temperature to adhere to the spunbond fibers of beams 2 and 4. According to an exemplary embodiment of the invention, rollers 10 and 12 may be a calender 10 having a bonding roll 12 defining a bond pattern. Alternatively, the web 6 may be ultrasonically bonded, chemically bonded, or through-air bonded. For example, an ultrasonic device or a through-air bonding device may be used in place of calender bonding rollers 10 and 12, such a device using air at elevated temperatures sufficient to cause thermal bonding between the filaments and/or fibers at their intersecting portions by melting the lower melt temperature polymeric component.

The nonwoven web 6 may be incorporated into a nonwoven laminate. The laminate may be formed through conventional means, including but not limited to thermal bonding, ultrasonic bonding, and/or chemical/adhesive bonding.

Figure 2:
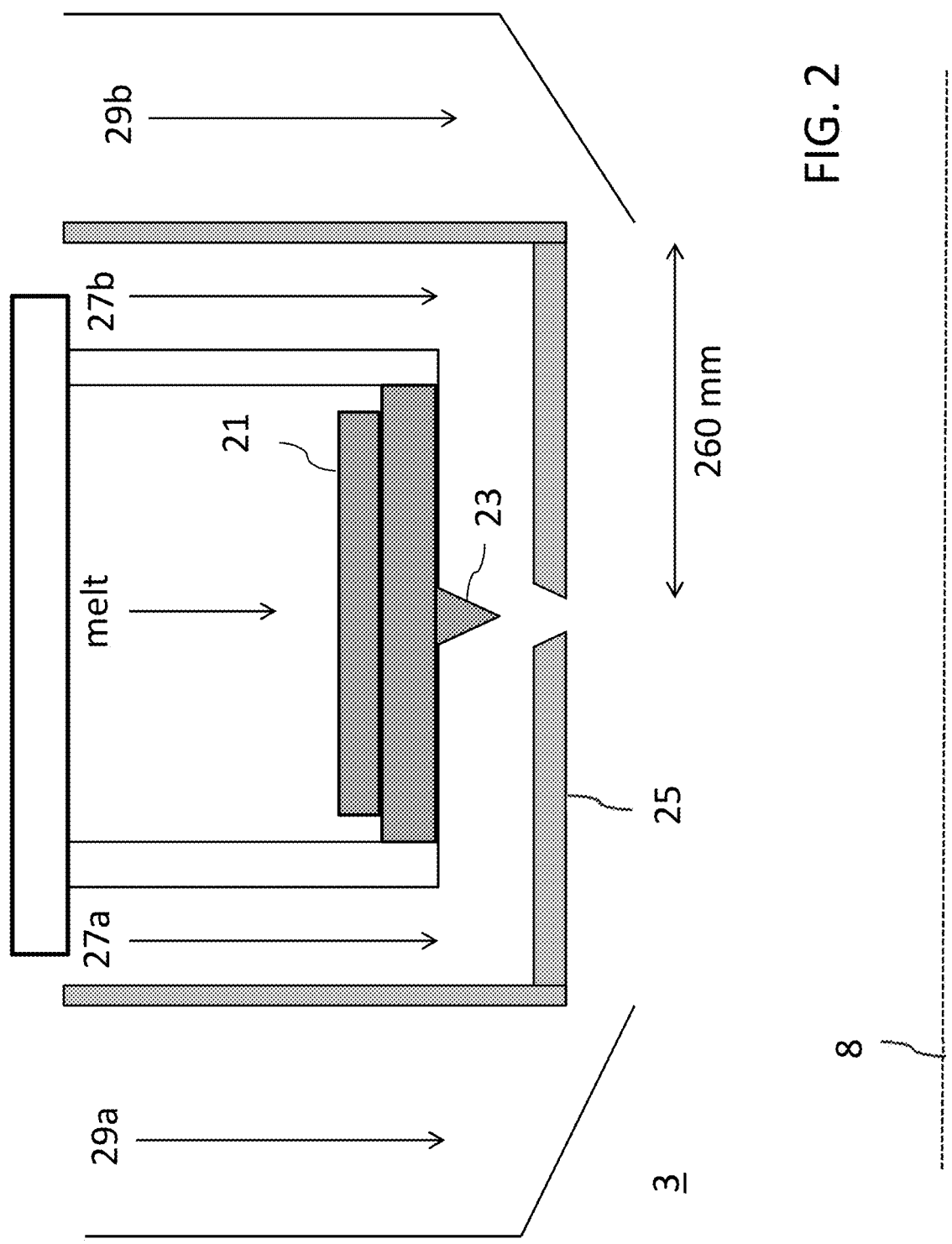
FIG. 2 is a representative cross-sectional diagram of a meltblown fiber apparatus ("beam") according to an exemplary embodiment of the present invention.

FIG. 2 illustrates a representative meltblown mechanism (or "beam") 3 (e.g., 3a-3d) in accordance with an exemplary embodiment of the invention. As shown in FIG. 2, meltblown beam 3 may comprise a breaker plate 21 and a die tip 23 to respectively receive and extrude a polymer melt that is streamed into an air knife 25 that directs high velocity gas (e.g. air) streams 27a and 27b to attenuate the stream of molten thermoplastic polymer material to reduce its diameter. In accordance with an exemplary embodiment of the invention, as shown in FIG. 2, meltblown beam 3 may comprise additional secondary air ducts that direct secondary high velocity air streams 29a and 29b to cool the fiber material. As described above, the meltblown fibers are quasi-randomly deposited by beams 3a-3d over the spunbond layer laid by spinning beam 2 on conveyor 8 to form a meltblown web. Again, beam 3a, and optionally beam 3d, may be configured to deposit a "coarse" MB fiber sublayer with fiber diameters above 2 microns and beams 3b and 3c are configured to deposit a "fine" MB fiber sublayer with fiber diameters at or below 2 microns.

FIG. 3 is a table of process parameters for the respective MB sublayers in accordance with an exemplary embodiment of the invention. As shown in FIG. 3, the MB sublayers may be formed using: a meltblown die with 35-75 holes per inch; meltblown capillary diameter at 0.3-0.4 millimeters (mm); meltblown die temperature at 250-280 degrees Celsius (° C.); meltblown polymer throughput rate at 20-60 kilograms per hour per meter (kg/hr/m); meltblown hot air temperature at 260-280° C.; meltblown hot air flow rate at 2600-4000 cubic meters per hour ($m^3$/hr); and meltblown secondary air cooling temperature at 20-30° C. According to a preferred embodiment, the meltblown die temperature may be between approximately 255° C. and 270° C.

FIG. 3 further illustrates exemplary process parameters for "coarse" and "fine" MB fiber sublayers. As shown in FIG. 3, the MB sublayers may be formed using: a meltblown die with 35 holes per inch; meltblown capillary diameter at 0.4 mm; meltblown die temperature at 255° C.; meltblown polymer throughput rate at 30 kg/hr/m; meltblown hot air temperature at 265 ° C.; meltblown hot air flow rate at 2600 $m^3$/hr; and meltblown secondary air cooling temperature at 20° C. Alternatively, the MB sublayers may be formed using: a meltblown die with a meltblown capillary diameter at 0.3 mm; meltblown die temperature at 255° C.; meltblown polymer throughput rate at 50 kg/hr/m; meltblown hot air temperature at 265° C.; meltblown hot air flow rate at 3900 $m^3$/hr; and meltblown secondary air cooling temperature at 30° C.

In an exemplary embodiment, a base fabric with an SMS structure includes an amount of meltblown fibers making up 2-45% of the total web by weight, preferably 16-33% of the total web by weight, and more preferably about 19-30% of the total web by weight.

Advantageously, the inner coarse fiber layer may slow down the passage of liquid because it disrupts the capillary network of the fine meltblown layers, thereby improving the barrier properties of the laminates.

FIG. 4A is a table of selective results for nonwoven fabric trials conducted in accordance with exemplary embodiments of the present invention. Examples of MB nonwovens with a "flat" MB profile (i.e., uniform fiber size layer) and ones with various plural meltblown sublayers ("hump," "modified hump," and "gradient" MB profiles) made in accordance with exemplary embodiments of the invention are included in the table illustrated in FIG. 4A. As reflected in FIG. 4A, materials used in the examples include meltblown fibers made from respective types of resin (A, B, and C). Resin A was a polypropylene homopolymer resin with a Melt Flow Rate (at 230° C/2.16 kg) (MFR) of 1300 g/10 min (per ASTM D1238) and a density of 0.90 g/$cm^3$ (per ASTM D1505). Resin B was a homopolymer resin with a MFR of 1800 g/10 min (per ASTM D1238) and a density of 0.90 g/$cm^3$ (per ASTM D792). Resin C was a metallocene-based homopolymer resin with a MFR of 1550 g/10 min. Specifically, for Resin A, Total™ PPH 3962 was used; for Resin B, lyondellbasell® Metocene MF650Y was used; and for Resin C, ExxonMobil® Achieve™ 6936G2 was used. A "hump" MB profile comprises a coarse fiber sublayer (>2 μm) between two fine fiber sublayers (≤2 μm), a "modified hump" MB profile comprises two coarse fiber sublayers (with different respective fiber diameters) between two fine fiber sublayers, and a "gradient" MB profile comprises coarse-to-fine sublayers.

As shown therein, samples are identified by a Trial number with a corresponding description of a basis weight (BW) of the nonwoven in gsm (grams per square meter), a number (#) MB beams (i.e., number of same or different sublayers), MB material (basis weight) in the nonwoven in gsm, a percentage (%) of MB fibers in the nonwoven, the MB resin used, an MB profile of the sublayers, a comparative Low Surface Tension Strike-through (LSTS) average test result in seconds, air permeability in $m^3$/min/$m^2$.

The LSTS parameter refers to an average low surface tension liquid strike-through time (LSTS) measure of the respective fabric sample, as measured using the Low Surface Tension Fluid Strikethrough Time Test procedure described in U.S. Patent Application Publication No. 2014/0272261 (Udengaard et al.), which is hereby incorporated by reference. In particular, the LSTS testing was performed following the procedure described in paragraphs [0153]-[0184] of Udengaard et al. Testing results were reported and averaged after all 30 tests were performed.

For each sample, air permeability (AP) was also tested in accordance with the ASTM D737-69 procedure.

LSTS of each sample was determined in accordance with the following test procedure:

Low Surface Tension Fluid Strikethrough Time Test

The low surface tension fluid strikethrough time test is used to determine the amount of time it takes a specified quantity of a low surface tension fluid, discharged at a prescribed rate, to fully penetrate a sample of a nonwoven substrate that is placed on a reference absorbent pad. As a default, this is also called the 32 mN/m Low Surface Tension Fluid Strikethrough Test because of the surface tension of the test fluid and each test is done on two layers of the nonwoven substrate sample simply laid on top of each other.

For this test, the reference absorbent pad is 5 plies of Ahlstrom grade 989 filter paper (10 cm.times.10 cm) and the test fluid is a 32 mN/m low surface tension fluid.

Scope

This test is designed to characterize the low surface tension fluid strikethrough performance (in seconds) of nonwoven substrates intended to provide a barrier to low surface tension fluids, such as mixtures of urine and bowel movements or runny bowel movements for example.

Equipment

Lister Strikethrough Tester: The instrumentation is the same as that described in EDANA ERT 153.0-02 section 6 with the following exception: the strike-through plate has a star-shaped orifice of 3 slots angled at 60 degrees with the narrow slots having a 10.0 mm length and a 1.2 mm slot width. The orifice 2000 is illustrated in FIG. 31. This equipment is available from Lenzing Instruments (Austria) and from W. Fritz Metzger Corp (USA). The unit needs to be set up such that it does not time out after 100 seconds.

Reference Absorbent Pad: Ahlstrom Grade 989 filter paper, in 10 cm.times.10 cm areas, is used. The average strikethrough time is 3.3+0.5 seconds for 5 plies of filter paper using the 32 mN/m test fluid and without the web sample. The filter paper may be purchased from Empirical Manufacturing Company, Inc. (EMC) 7616 Reinhold Drive Cincinnati, Ohio 45237.

Test Fluid The 32 mN/m surface tension fluid is prepared with distilled water and 0.42+/−0.001 g/liter Triton-X 100. All fluids are kept at ambient conditions. Electrode-Rinsing Liquid: 0.9% sodium chloride (CAS 7647-14-5) aqueous solution (9 g NaCl per 1 L of distilled water) is used.

Test Procedure

Ensure that the surface tension is 32 mN/m+/−1 mN/m according to the Surface Tension of a Liquid test described herein. Otherwise remake the test fluid.

Prepare the 0.9% NaCl aqueous electrode rinsing liquid.

Ensure that the strikethrough target (3.3+/−0.5 seconds) for the Reference Absorbent Pad is met by testing 5 plies with the 32 mN/m test fluid as follows:

Neatly stack 5 plies of the Reference Absorbent Pad onto the base plate of the strikethrough tester.

Place the strikethrough plate over the 5 plies and ensure that the center of the plate is over the center of the paper. Center this assembly under the dispensing funnel.

Ensure that the upper assembly of the strikethrough tester is lowered to the pre-set stop point.

Ensure that the electrodes are connected to the timer.

Turn the strikethrough tester "on" and zero the timer.

Using the 5 mL fixed volume pipette and tip, dispense 5 mL of the 32 mN/m test fluid into the funnel.

Open the magnetic valve of the funnel (by depressing a button on the unit, for example) to discharge the 5 mL of test fluid. The initial flow of the fluid will complete the electrical circuit and start the timer. The timer will stop when the fluid has penetrated into the Reference Absorbent Pad and fallen below the level of the electrodes in the strikethrough plate.

Record the time indicated on the electronic timer.

Remove the test assembly and discard the used Reference Absorbent Pad. Rinse the electrodes with the 0.9% NaCl aqueous solution to "prime" them for the next test. Dry the depression above the electrodes and the back of the strikethrough plate, as well as wipe off the dispenser exit orifice and the bottom plate or table surface upon which the filter paper is laid.

Repeat this test procedure for a minimum of 3 replicates to ensure the strikethrough target of the Reference Absorbent Pad is met. If the target is not met, the Reference Absorbent Pad may be out of spec and should not be used.

After the Reference Absorbent Pad performance has been verified, nonwoven substrate samples may be tested.

Cut the required number of nonwoven substrate specimens. For nonwoven substrates sampled off a roll, cut the samples into 10 cm by 10 cm sized square specimens. For nonwoven substrates sampled off of a consumer product, cut the samples into 15 by 15 mm square specimens. The fluid flows onto the nonwoven substrate specimen from the strike through plate.

Touch the nonwoven substrate specimen only at the edge.

Neatly stack 5 plies of the Reference Absorbent Pad onto the base plate of the strikethrough tester.

Place the nonwoven substrate specimen on top of the 5 plies of filter paper. Two plies of the nonwoven substrate specimen are used in this test method. If the nonwoven substrate sample is sided (i.e., has a different layer configuration based on which side is facing in a particular direction), the side facing the wearer (for an absorbent product) faces upwards in the test.

Place the strikethrough plate over the nonwoven substrate specimen and ensure that the center of the strikethrough plate is over the center of the nonwoven substrate specimen. Center this assembly under the dispensing funnel.

Ensure that the upper assembly of the strikethrough tester is lowered to the pre-set stop point.

Ensure that the electrodes are connected to the timer. Turn the strikethrough tester "on" and zero the timer.

Run as described above.

Repeat this procedure for the required number of nonwoven substrate specimens. A minimum of 5 specimens of each different nonwoven substrate sample is required. The average value is the 32 mN/m low surface tension strikethrough time in seconds.

Figure 5A:
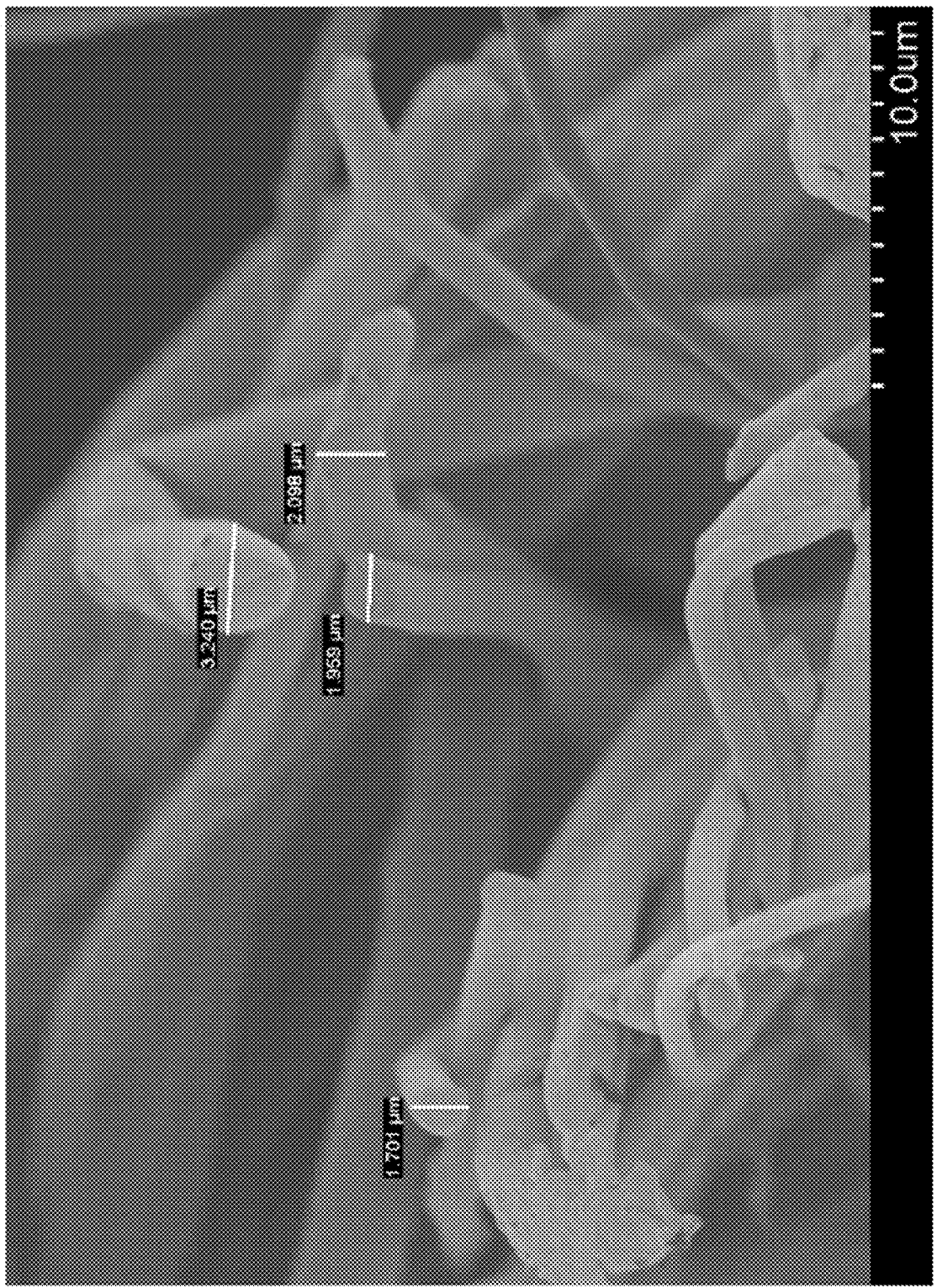
FIGS. 5A, 5B, and 5C are micrographs of nonwoven fabrics that are produced under process parameters and conditions reflected in FIG. 3 in accordance with exemplary embodiments of the present invention.
Figure 5B:
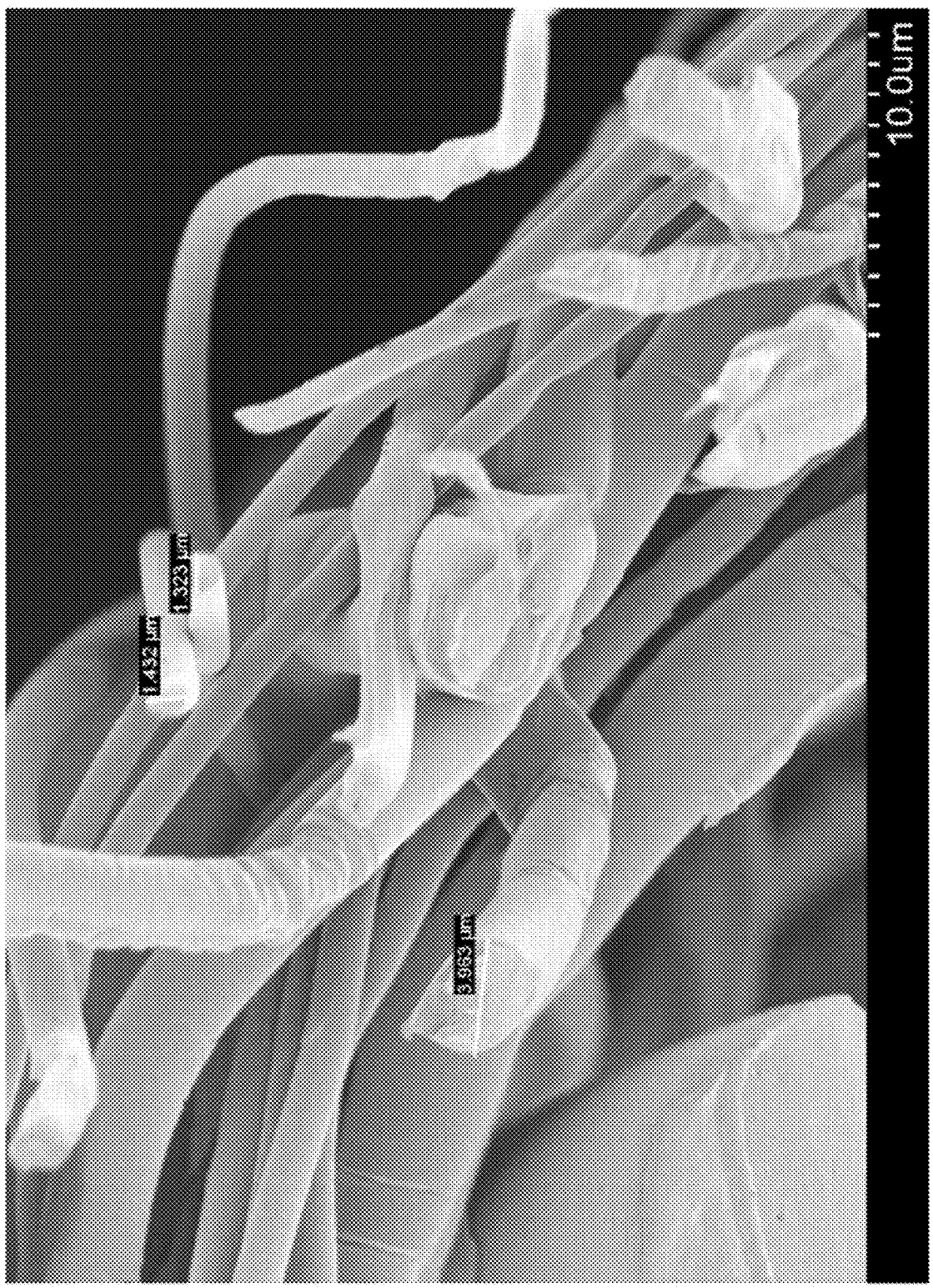
Figure 5C:
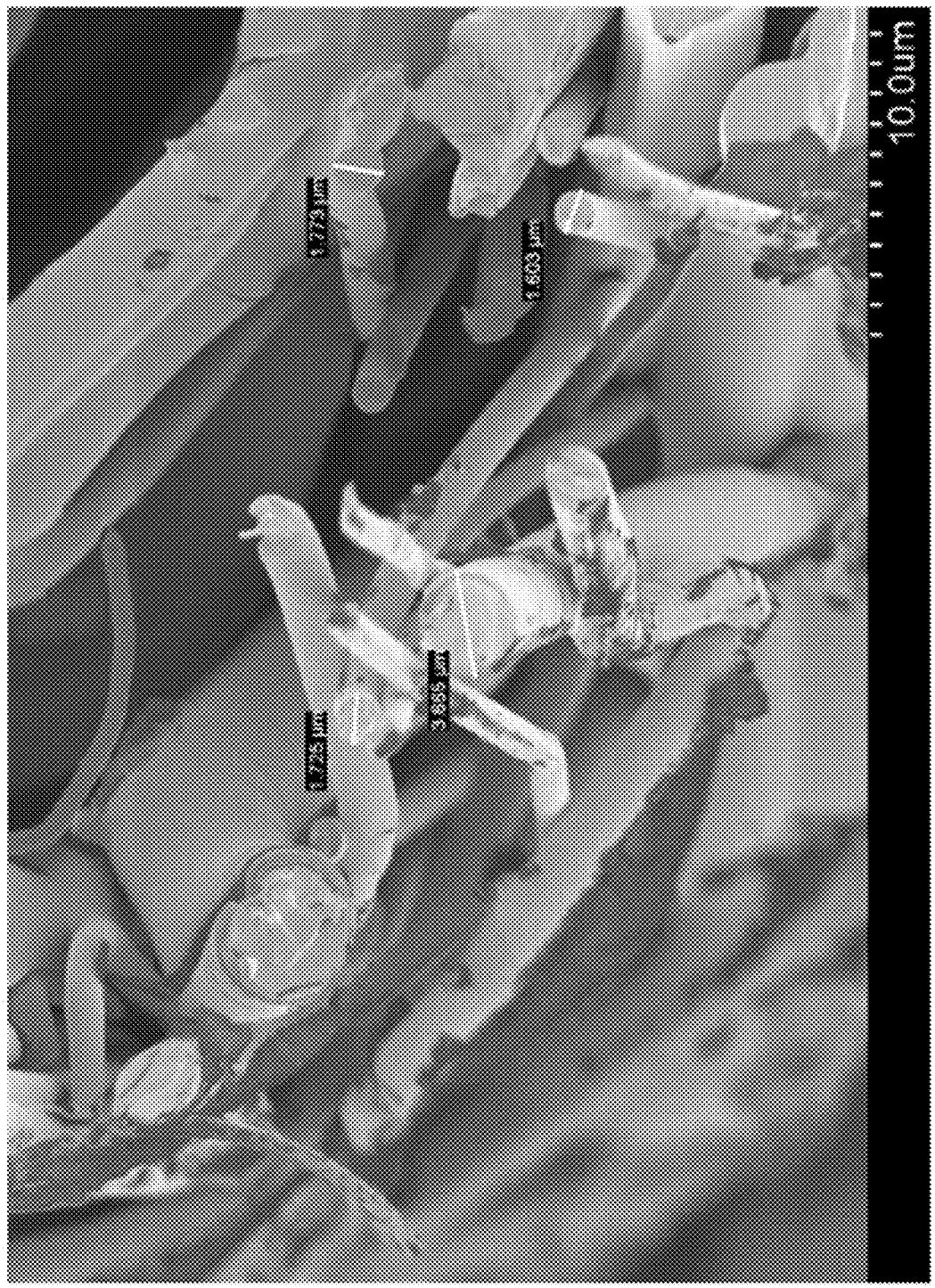

FIGS. 5A, 5B, and 5C are micrographs of nonwoven fabrics that have been formed with "coarse" and "fine" MB sublayers under process parameters and conditions reflected in FIGS. 3 and 4 in accordance with exemplary embodiments of the present invention. In particular, FIGS. 5A, 5B, and 5C are micrographs of nonwovens from trial 22 identified and reflected in FIG. 4 (EXAMPLE 4). As shown in FIGS. 5A-C, the nonwovens comprise particularly desirable layering of the coarse and fine MB sublayers, with a difference in measured fiber diameters between the coarse and fine MB sublayers being between approximately 1.1 to 2.7 microns.

Figure 6A:
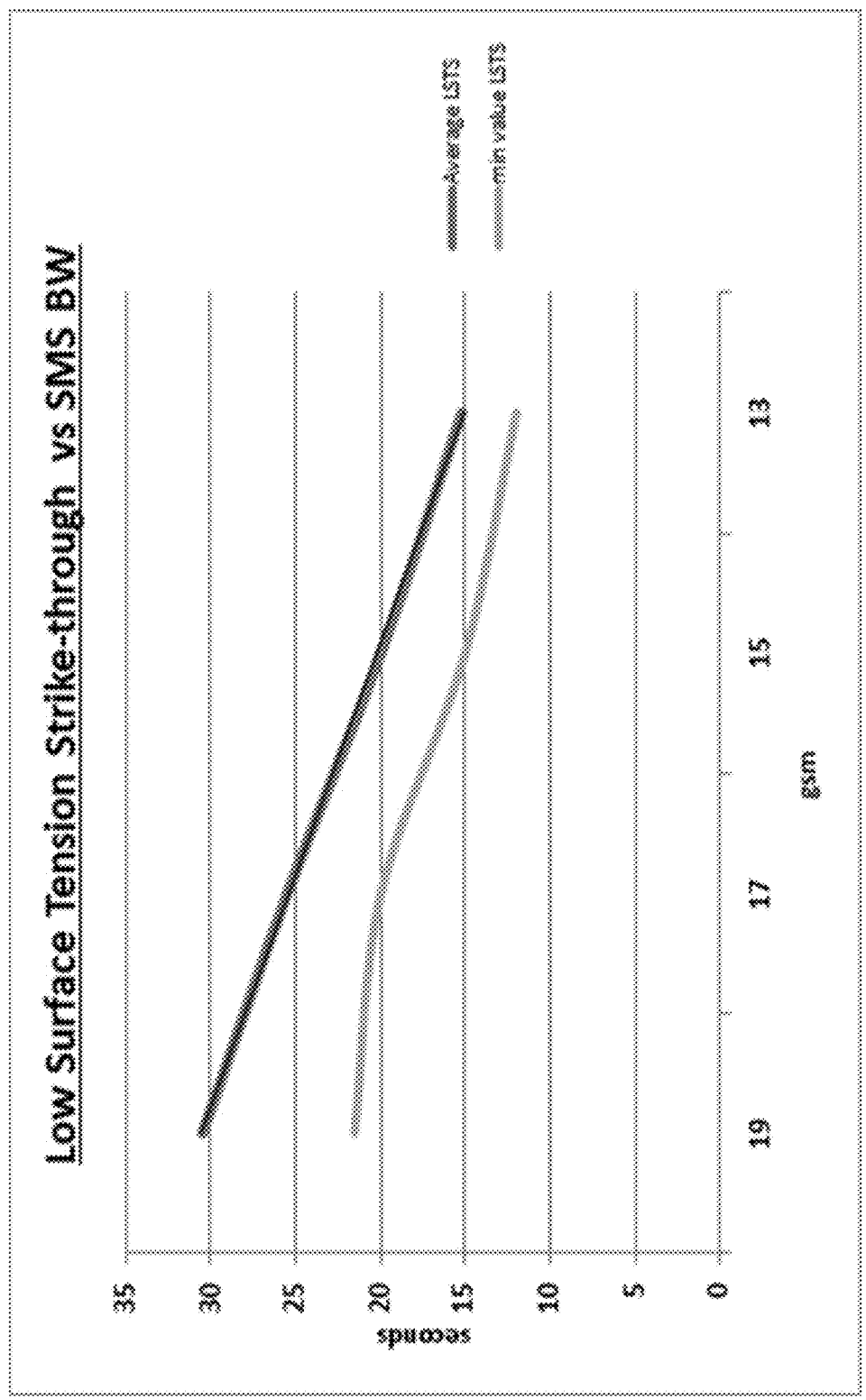
FIGS. 6A, 6B, 6C, 6D, and 6E are graphs illustrating correlations between various parameters among the results shown in FIG. 4 in accordance with exemplary embodiments of the present invention.
Figure 6B:
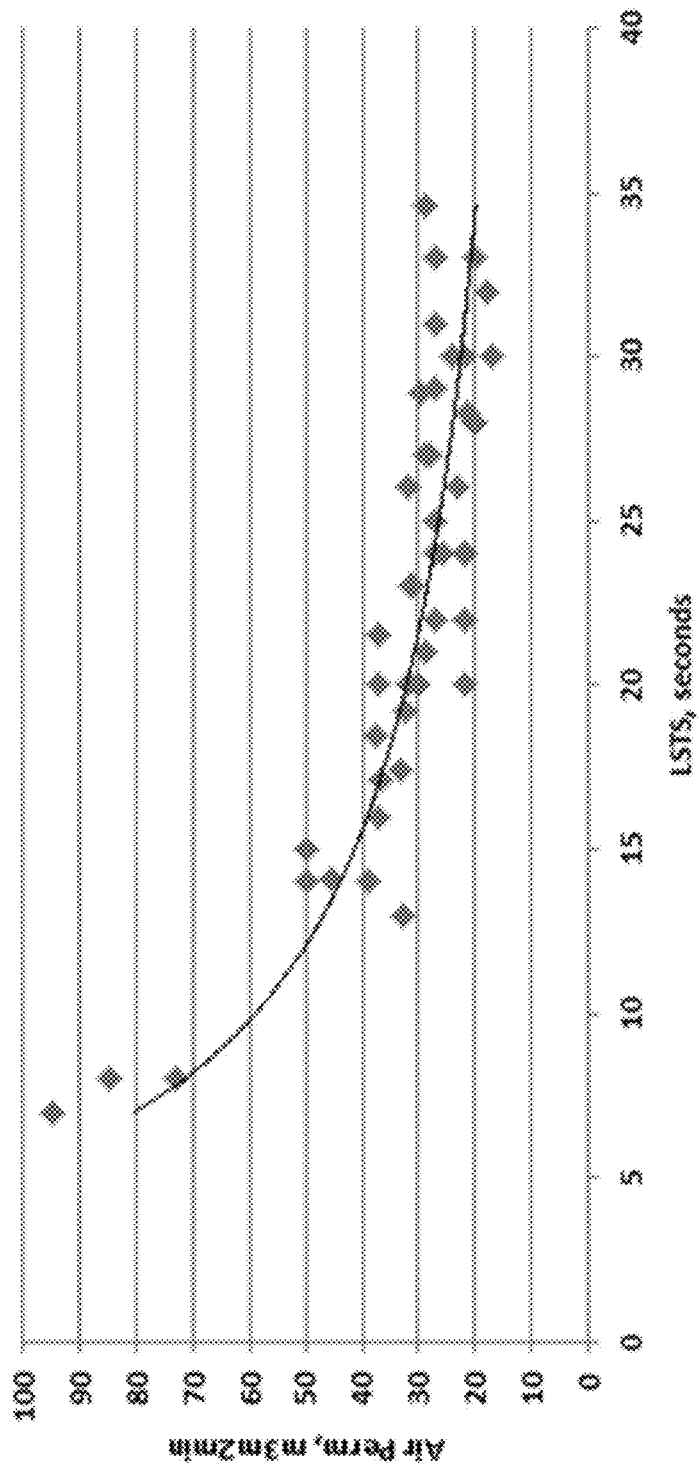
Figure 6C:
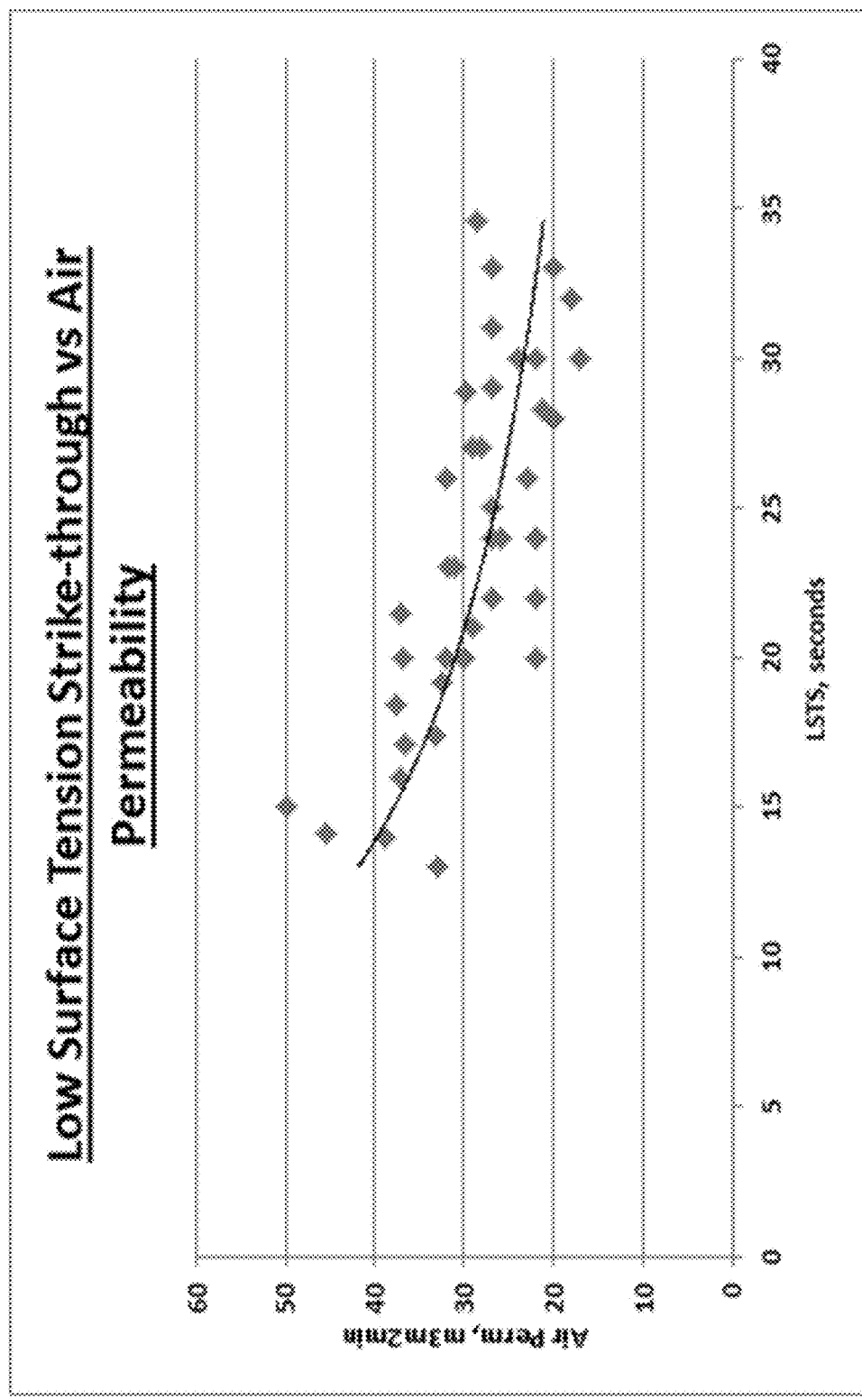
Figure 6D:
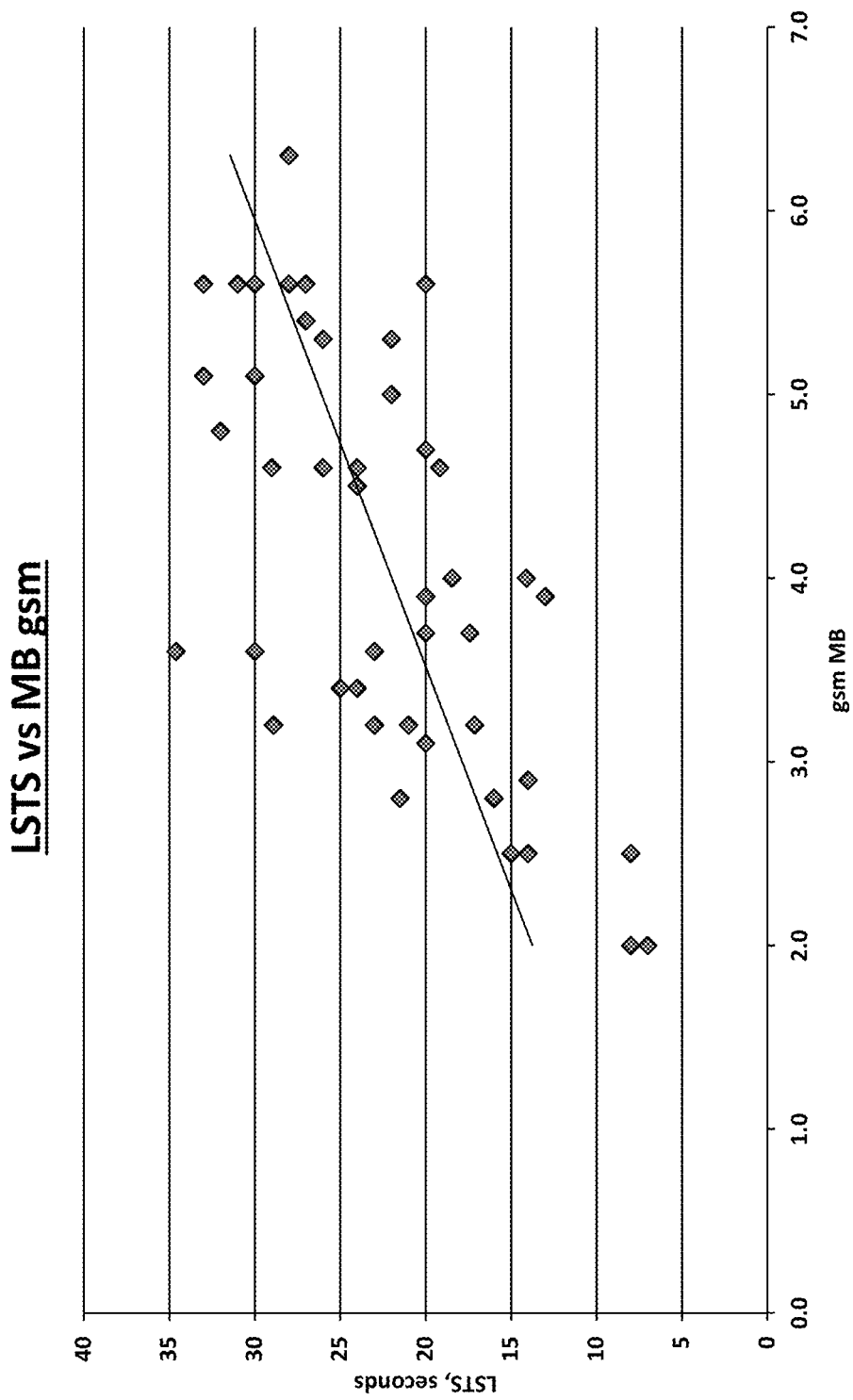
Figure 6E:
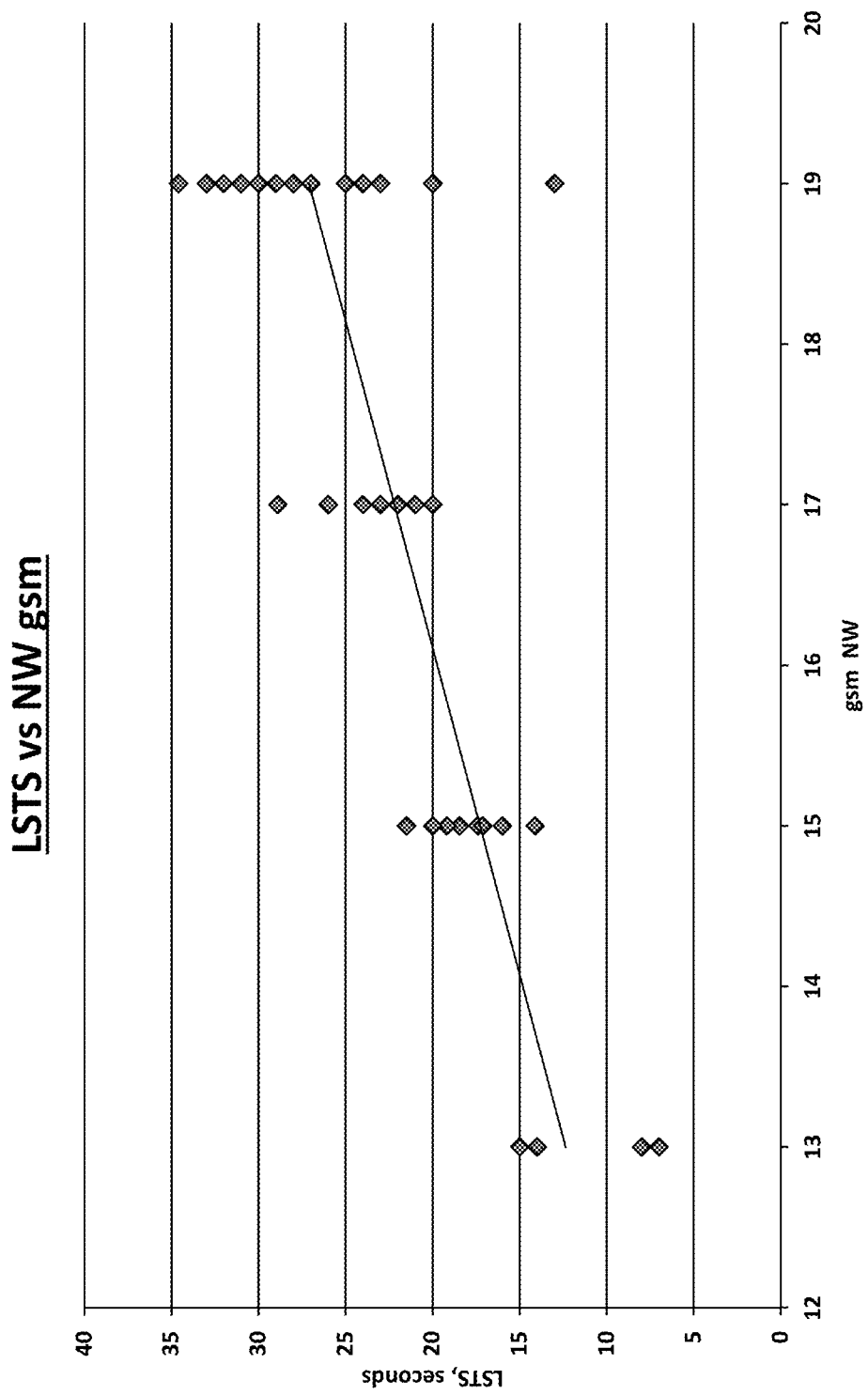

FIGS. 6A, 6B, 6C, 6D, and 6E are graphs illustrating correlations between various parameters of the trials conducted under process parameters and conditions reflected in FIG. 4A in accordance with exemplary embodiments of the present invention. In particular, FIG. 6A illustrates the correlation between average LSTS performance and basis weight of the trial fabrics listed in FIG. 4A as compared to: a minimum LSTS value vs. basis weight among the trial results. FIG. 6B illustrates the correlation between air permeability and LSTS among the trial results in FIG. 4A. FIG. 6C illustrates the correlation between air permeability and LSTS among the trial results in FIG. 4A without control trials 1-3. FIG. 6D illustrates the correlation between LSTS and the basis weight of the MB fibers within the fabrics for the respective trials in FIG. 4A. FIG. 6E illustrates the correlation between LSTS and the net weight (NW), or basis weight, of the nonwoven fabric of the respective trials in FIG. 4A. It should be appreciated that FIGS. 6A-6E illustrate effectiveness of the "hump" profile.

Other approaches to using meltblown layers to achieve good barrier properties are known. For example, very fine fibers (often called nanofibers) or a combination of fibers with differing levels of fineness may be used to create a barrier layer (as described in, for example, US20180178486 filed by PEGAS NONWOVENS). These known methods achieve effective barrier properties by adjusting median or average fiber diameter values within the meltblown layers, but do not directly address fiber diameter distribution.

The term "fiber diameter distribution" or "fiber distribution" as used herein relates to the degree of fiber diameter variability in one meltblown layer. A person skilled in the art will appreciate that a meltblown production beam produces fibers from very fine (e.g., diameters below 2 microns) to rather coarse (e.g., diameters over 5 microns). To describe the fiber thickness in the layer usually the average or median value is used. Averages are useful for simplification, but simplification in this context does not lead to optimization of barrier properties. In this regard, with reference to FIGS. 7 and 8, a meltblown layer with fibers having an average diameter of 2 microns can be, for example, a layer with 80% of fibers in the range 1.75-2.25 microns (as indicated by the dashed line curved in FIG. 7), or for example a layer with just 20% fibers in this area (as indicated by the solid line curve in FIG. 7).

Figure 7:
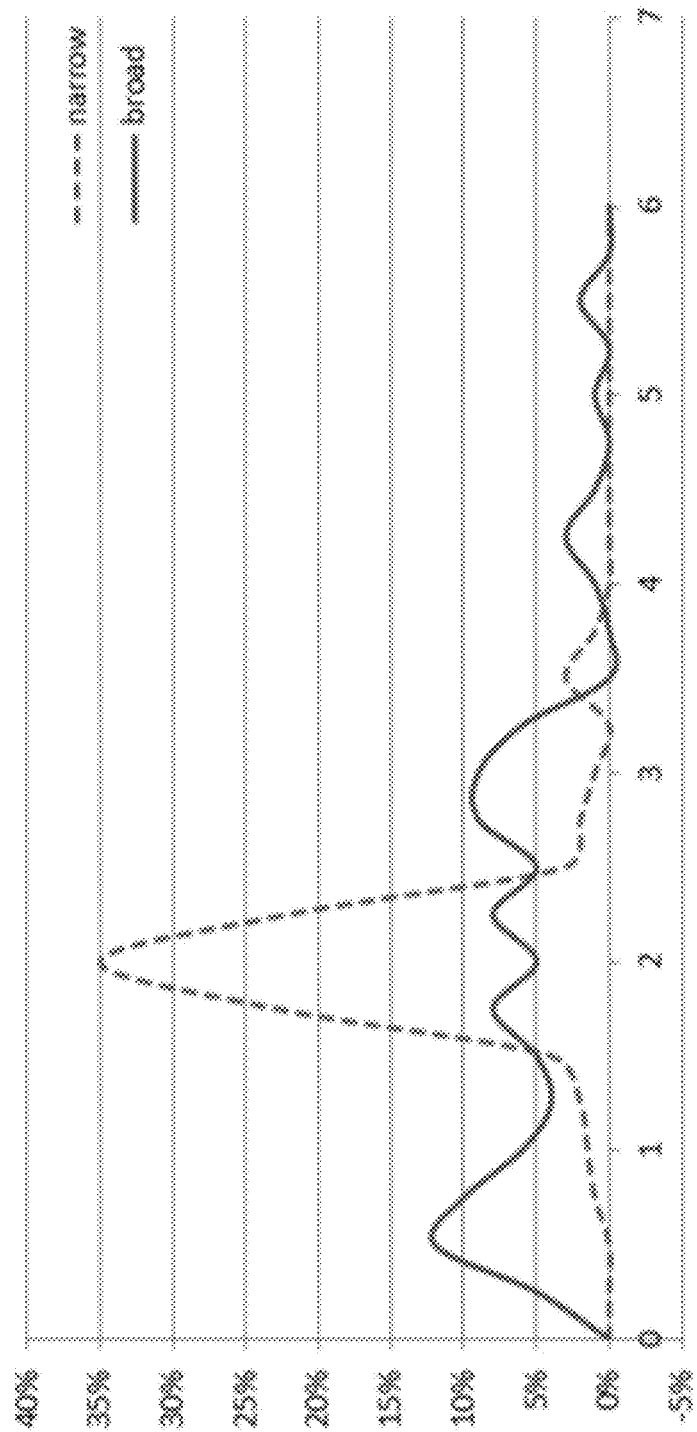
FIG. 7 is a chart showing distribution of fiber diameters within a meltblown layer.
Figure 8:
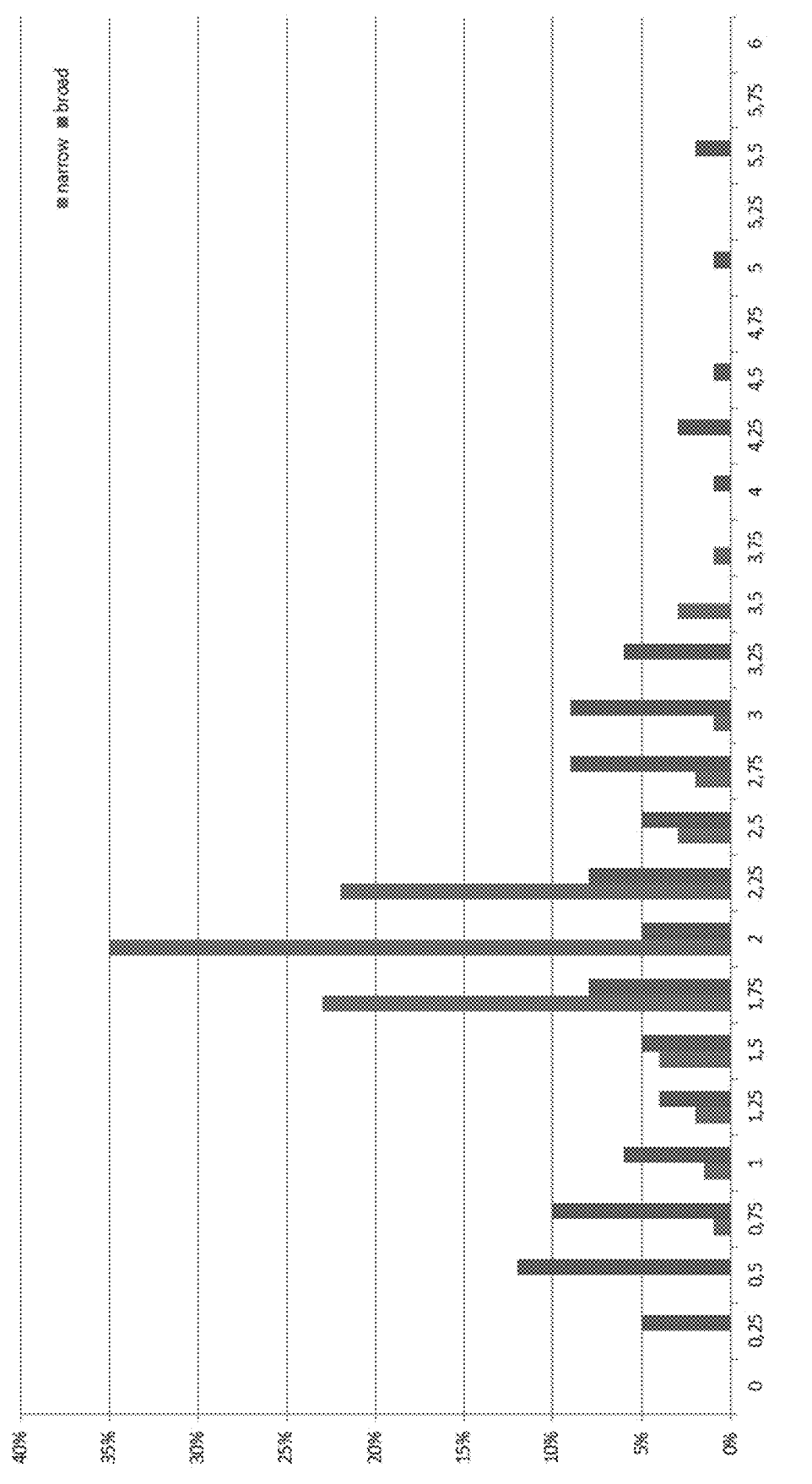
FIG. 8 is a histogram showing distribution of fiber diameters within a meltblown layer.

As can be seen in FIGS. 7 and 8, the average value is in fact not very frequent in the material (only 5% of the fibers for the broad distribution) and the most frequent increments are located rather far from each other. For a broad distribution, there is typically a rather large content of very fine fibers and also a rather large content of coarse and very coarse fibers. In comparison, the narrow distribution creates one large peak with one increment or frequent increments adjacent to each other.

For the purposes of the present invention, to determine the fiber thickness distribution of a meltblown layer, at least 100 fiber thicknesses are measured in a sample. The results are set to 0.25 micrometre increments (forming a histogram). The fiber frequency within a given increment is recalculated into a percentage ratio. The increments can be shown in a plot (see FIG. 7).

For example, if 23 fiber measurements are within the increment 1.25-1.50 micron, and the total amount of measured fibers is 100, the percentage ratio is 23% (23/100).

For the purpose of the present disclosure, fiber thickness distribution is defined as follows:

Narrow fiber thickness distribution (N) has at least one peak equal to or over 30% frequency level. That is, at least one increment is equal to or higher than 30%. Alternatively, a narrow fiber thickness distribution (N) has at least one peak equal to or over 20% and no other peak over 5%. That is, at least one increment is equal to or over 20% and the adjacent increments are equal or lower and the further adjacent increments are equal or lower, etc., and when an increment is not equal or lower than its neighbour so as to form a local peak, than that increment is lower than 5%.

Middle fiber thickness distribution (M) has at least one peak equal to or over 20% and some other peak over 5%. That is, at least one increment is equal to or over 20% and the adjacent increments are equal or lower and the further adjacent increments are equal or lower, etc., and when an increment is not equal or lower than its neighbour so as to form a local peak, than that increment is higher than 5%.

Broad fiber thickness distribution (B) has no peak equal or over 20%. That is, no increment is equal or over 20%.

Layers with differing fiber diameter distributions will have very different characteristics. For example, the pore characteristics will be different for broad and for narrow distributions, and any agent (e.g., gas or liquid) flowing through the fabric will act differently. Without being bound by theory, a layer with narrow fiber thickness distribution (N) will tend to have a more regular pore arrangement with very small pores as compared to layers with broader fiber thickness distribution (M, B). On the contrary, a layer with broad fiber thickness distribution (B) will tend to have more irregular (i.e., less regular) pore arrangement as compared to layers with narrower fiber thickness distribution (M, N). In B layers, more coarse fibers can form in a sense an inner structure and smaller fibers can form "bridges" between coarse fibers, filling the larger pores between the coarse fibers. Also, in B layers, the pore "path/route" can be expected to be more irregular.

Surprisingly, the inventors of the present application have found that a combination of layers with differing distributions of fiber diameter values brings an advantage to laminate barrier properties. Without being bound by the theory, the different characteristics of the N, M and B layers, especially the differing characteristics of the capillary network in each layer, results in the border between these layers disrupting the entire laminate capillary network, thereby slowing down or blocking the passage of medium (e.g., gas, liquid, etc.) through the laminate.

In accordance with an exemplary embodiment of the present invention, a composite nonwoven web includes at least three meltblown layers with differing fiber thickness distributions. At least two meltblown layers have a narrow (N) or a medium (M) fiber thickness distribution and at least one meltblown layer has a medium (M) or a broad (B) fiber thickness distribution. The layers are combined so that the layer with medium (M) or broad (B) fiber thickness distribution is located in between the two layers with narrow (N) or medium (M) fiber thickness distribution, where the outer layers have a narrower fiber thickness distribution than the middle layer (e.g., NMN, NBN, MBM compositions) forming a so-called "distribution hump" profile ("D-hump"). Preferably the layers are combined so that the layer with medium (M) or broad (B) fiber thickness distribution is in the middle between two layers with narrow (N) fiber distribution, thereby forming a NMN or NBN composition.

Preferably the fiber thickness distribution in adjacent layers forming the "D-hump" profile differ by an increment coefficient of at least 1, more preferably by at least 1.5.

Increment coefficient is a value expressing the broadness of the distribution of 50% of the most frequent measured values within the sample. Measured values are sorted to increments (increments of 0.25 micron). In order to determine increment coefficient, the increments are sorted according to the amount of values in each, from the most frequent to the less frequent, and the number of increments containing 50% of the most frequent measured values is counted. For example, the narrow distribution shown in FIG. 7 with 200 measured values has the most frequent increment containing 70 measured values, and the second most frequent increment containing 46 measured values. Together they contain more than 50% of the most frequent measured values by an amount of 30 values (70+46 =116, which is 16 values over the 100 values which make up the 50% of values). Thus, we are concerned in this example only with 30 of the values from the 46 value increment. The increment coefficient is then 1.65(=1+(46−30)/46)). The increment coefficient for the broad distribution shown in FIG. 7 is 5.75.

In exemplary embodiments, the meltblown part of a laminate can be formed from more than three layers. Other melt blown layers may be added on one or both sides of the three-layer meltblown portion of the laminate, such as, for example, at one or both outer sides of the laminate. The added meltblown layers can have various properties. The sequence can be repeated (e.g., NMNMN, NBNBN) and/or any part can be doubled or tripled (e.g. NNMNN, NNBNN, NNNMNNN, NNNBNNN). One of ordinary skill in the art would appreciate that other variations are possible in accordance with exemplary embodiments of the present invention, such as, for example, NNMNBN, NBNMN, . . . etc.

In exemplary embodiments, a series of adjacent layers do not follow an increasing fiber thickness distribution (e.g., NMB), but instead the layers within the sequence switch between narrower and broader distribution (e.g., NMN, NMNBNMN, etc.)

Without being bound by theory, it is believed that the inventive multilayer structure provides a barrier for gasses (inert to polymers forming the layer) mainly due to the capillary network and toughness of the fiber structure. The narrower and more tortuous the capillary network, the slower the gas flow through the fabric. The toughness of the fabric structure blocks the gas from forming wider channels. The D-hump profile, with capillary disruptions and different capillary network characteristics, provides enhanced barrier properties as compared to a "flat" profile, as can be seen for example in regards to the air permeability results.

A meltblown barrier layer according to exemplary embodiments of the invention with a basis weight below 1 gsm provides a maximum air permeability of 70 m³/min/m².

A meltblown barrier layer according to exemplary embodiments of the invention with a basis weight over 1 gsm provides a maximum air permeability of 65 m³/min/m².

A meltblown barrier layer according to exemplary embodiments of the invention with a basis weight over 2 gsm provides a maximum air permeability of 57 m³/min/m².

A meltblown barrier layer according to exemplary embodiments of the invention with a basis weight over 3 gsm provides a maximum air permeability of 38 m³/min/m².

A meltblown barrier layer according to exemplary embodiments of the invention with a basis weight over 4 gsm provides a maximum air permeability of 27 m³/min/m².

A meltblown barrier layer according to exemplary embodiments of the invention with a basis weight over 5 gsm provides a maximum air permeability of 20 m³/min/m².

A meltblown barrier layer according to exemplary embodiments of the invention with a basis weight over 7 gsm provides a maximum air permeability of 15 m³/min/m².

Without being bound by theory, it is believed that the inventive multilayer structure provides a barrier for liquids due to two main principles: the relation of liquid and fiber surface tension and the fiber structure with typical capillary network. If the fiber surface tension is lower than liquid surface tension, the fiber is so called "phobic" and forms the barrier by negative capillary effect. The higher this difference, the stronger is the negative capillary effect and also the barrier. For example, water, as a polar liquid, is well repelled by nonpolar polyolefin fiber. On the other hand, the various body liquid exudates can have surface tension energy closer to that of the polyolefin fiber and so the repelling or barrier effect is decreased. The smaller the fiber—liquid surface tension difference, the lower is the capillary effect (positive or negative), and thus the characteristics of the capillary network becomes more important in accordance with principles similar to those as described for gas. In this regard, the "D-hump" profile, with capillary disruptions and differing capillary network characteristics, provides enhanced barrier properties, especially for lower surface tension liquids, as compared to a "flat" profile, as can be seen for example in regards to the Low Surface Tension Fluid Strikethrough Time (LSTS) results.

A meltblown barrier layer according to exemplary embodiments of the invention with a basis weight below 1 gsm provides an LSTS of at least 6 seconds.

A meltblown barrier layer according to exemplary embodiments of the invention with a basis weight over 1 gsm provides an LSTS of at least 7 seconds.

A meltblown barrier layer according to exemplary embodiments of the invention with a basis weight over 2 gsm provides an LSTS of at least 9 seconds.

A meltblown barrier layer according to exemplary embodiments of the invention with a basis weight over 3 gsm provides an LSTS of at least 17 seconds.

A meltblown barrier layer according to exemplary embodiments of the invention with a basis weight over 4 gsm provides an LSTS of at least 22 seconds.

A meltblown barrier layer according to exemplary embodiments of the invention with a basis weight over 5 gsm provides an LSTS of at least 25 seconds.

Further, the thicker fibers in the layer with medium or broad distribution can serve as an inner "bracing" or "skeleton" and can slightly increase the toughness of a fabric. Strengthening of the structure can increase its resistance against pressure caused by a medium (gas, liquid) and can increase the threshold at which the barrier layer becomes mechanically damaged and loses its barrier properties.

The delicateness of melblown layers can be shown for example on water column results, where it is believed, without being bound by theory, the negative capillary effect strains the fibers and entire fiber structure so much, that the fiber structure is damaged before the benefit of the "D-hump" profile can be seen.

It is well known that the fiber thickness is very important for fabric barrier properties. Current standard meltblown fiber layers have in general average fiber diameters in the range of 2 to 5 microns. Fibers below 2 microns are considered fine fibers. As explained above, the fiber layer structure is very important for the barrier properties. The distribution of fiber thicknesses in the layer can significantly affect the fiber layer composition. For example, a theoretical fiber coefficient may be used to express the difference.

The term "theoretical fibre packing density coefficient" or "TCC" (theoretical cover coefficient) represents the coverage of a specific measuring unit by fibres and is dependent on the basis weight, density of the material forming the fibre and the cross-section of fibres contained in the nonwoven textile. TCC can thereby be visualised by imagining that from the entire mass contained in the assumed nonwoven textile, a single fibre is created with a circular cross-section corresponding to the median fibre diameter in the layer and that this fiber is then laid out on a surface in such a way that the fibers do not cross over or otherwise overlap. The proportion of the covered area then forms the TCC. The finer the fibres, with all other values remaining constant, the greater is the TCC, and similarly, TCC declines with an increasing density of the material that forms the fibre (with all other values remaining constant).

The TCC is calculated according to the following formula:

"theoretical cover coefficient" (TCC) $\% = d*L*100\%$;

$L = 4V/\pi d^2$ $V = m/p$ thus: $TCC \% = (4*m*100\%)/(\pi*p*d)$ d . . . =median of fiber thickness within the relevant layer (micron=1 e10⁻⁶ m)

L . . . length of fiber in 1 m² of textile (m/m²)

V . . . volume of fiber in 1 m² of textile (m3/m²)

m . . . mass of fiber in 1 m² of textile (g/m², corresponds to basis weight of relevant layer)

p . . . fiber density (mass g/volume cm³; corresponds to the density of the material from which the fiber is produced)

For example, the materials with distribution presented in FIGS. 7 and 8, produced from polypropylene, have the same average fiber thickness (2 microns), their median fiber thickness differs (2.00 for narrow and 1.75 micron for broad) and their TCC values for 1 gsm MB is 68% for narrow and 78% for broad distribution.

If the amount of fibers forming the layer is too small, then the fibers are deposited far from one another and the porosity of the layer is greater than would correspond to the diameter of the fibres. Without being bound by theory, we assume that the critical threshold for achieving the required barrier properties is, in the case of single layer, a coverage of at least 70%, preferably a coverage of 130% according to the "theoretical cover coefficient (TCC)" and at least 20% coverage for each layer, better yet 25% coverage for each layer, preferably at least 30% coverage for each layer in the case of the described combination of layers N and B or N and M or M and B, where mutual synergies may occur—especially concerning the capillary network distrubtion. It still, nevertheless, applies that the sum of the TCC values for meltblown barrier layers is at least 50%, better yet at least 60%, better yet at least 70%, preferably at least 100%.

An upper limit for the basis weight is not, from the viewpoint of the functionality of the invention, limited and a person skilled in the art will easily understand that with a growing % of coverage according to TCC, the barrier of the individual layers increases and a relative reduction of the described increase in barrier properties may occur as a result of the combination of layers according to the invention.

Without being bound by theory, it is assumed that the upper limit in the area particularly suitable for the implementation of the invention is perceptible up to a TCC of no more than 800% for every layer, better yet no more than 600% for every layer, better yet no more than 400% for every layer and preferably no more than 200% for every layer in the case of the described N, M and B layer combinations, where mutual synergies may occur.

As described previously, the "D-hump profile" relates to a combination of layers with differing fiber thickness distributions. In exemplary embodiments, the layers combined in the composition can have the same average or median fiber thickness. For example, Trail Nos. 25, 26 and 29 shown in FIG. 4 involved layers having the same average fiber.

For example, the N and M or N and B or M and B layers can have the same or very similar average fiber thickness.

For example, the N and M or N and B or M and B layers can have an average fiber thickness below 2 microns.

For example, the N and M or N and B or M and B layers can have an average fiber thickness below 1.5 microns.

For example, the N and M or N and B or M and B layers can have an average fiber thickness below 1 micron.

The "D-hump profile" can also have different average or median fiber thickness. In this regard, a strong synergy effect occurs when the D-hump profile is combined with difference in average fiber thickness between layers. Preferably, the narrow fiber thickness distribution layer (N, M) is formed by finer fibers (average or median) and the broader thickness distribution (M, B) is formed by coarser fibers.

As an example, a multilayer composition may be made up of 3 layers formed by 3 identical meltblown beams following each other.

For the purpose of this example, we assume that polymer throughput through the beam is linked to fiber distribution. The first and last beam are set on low throughput to produce fine fibers with narrow distribution. The middle beam is set on high throughput to produce fibers with broader distribution and higher average or median fiber thickness. The result is an NMN or NBN structure where the N layers has lower average fiber diameter than the M or B layers.

In other examples, each beam within a set of meltblown beams is optimised to obtain a desired layer fiber thickness and distribution (e.g., polymer type, polymer meltflow rate index and other properties, polymer throughput, polymer temperature, air temperature and volume, DCD, suction etc.). Many D-hump profile combinations according to the invention can be produced on such a line.

FIG. 4B provides further data in regards to Trial Nos. 1-47 showing the effect of the "D-hump" profile, along with new Trial Nos. 50-52. Trial Nos. 4, 5, 6, 8, 9, 10, 11, 14, 15, 16, 17, 18, 19, 21, 22, 23, 24, 32, 38, 43, 46, 47 and 50 shown in FIG. 4B exhibit the synergy effect of implementing both "D-hump" and "hump" profiles.

For example, the N layers can have an average fiber thickness below 2 microns and the B layers can have an average fiber distribution over 2 microns.

For example, the N layers can have an average fiber diameter below 1.5 micron and the M layer can have an average fiber thickness below 2 microns.

For example, the N, M or B layers can have an average fiber diameter below 2 microns.

For example, the N, M, B layers can have an average fiber thickness below 2 micron with the B layer having the coarsest fibers and the N layer having the finest fibers.

For example, each N, M or B layer in the composition can have differing average fiber thicknesses.

The inventors have found that the relative amount of the layer with narrower fiber distribution in the composition also provides a surprising effect. In this regard, the multilayer composition according to an exemplary embodiment of the present invention can be formed from three types of layer combinations as follows:

When the D-hump profile is made up of N and M layers, the N layer preferably forms at least 15 weight % of the meltblown layers of the composition, preferably 20 weight % of the meltblown layers of the composition, more preferably 25 weight % of the meltblown layers of the composition, even more preferably 30 weight % of the meltblown layers of the composition.

When the D-hump profile is made up of M and B layers, the M layer preferably forms at least 20 weight % of the meltblown layers of the composition, more preferably 25 weight % of the meltblown layers of the composition, even more preferably 30 weight % of the meltblown layers of the composition.

When the D-hump profile is made up of N and B layers, the N fibers preferably form at least 20 weight % of the meltblown layers of the composition, more preferably 25 weight % of the meltblown layers of the composition, more preferably 30 weight % of the meltblown layers of the composition Layers made from fine fibers (average fiber thickness below 2 microns) provide a high amount of fiber surface per one weigh unit and also high levels of capillary structure complexity where the capillary effect (both positive or negative) is stronger than for coarser fibers. The D-hump profile in such layers can be created from relatively small amount of polymer with considerable increase of barrier effect, especially in regards to LSTS and air permeability. For example, a layer formed from 1 micron fibers with narrow distribution reaches TCC 20% at 0.15 gsm and TCC 30% at 0.21 gsm basis weight. A broad distribution layer will need more polymer to provide the same coverage, but it can easily reach TCC 20% at a basis weight of 0.25 gsm and TCC 30% at a basis weight of 0.40 gsm. In accordance with exemplary embodiments, a D-hump profile with total TCC 70% can have a total basis weight of 0.61 gsm (0.15+0.25+0.21) and a D-hump profile with total TCC 100% can have total basis weight of 0.91 gsm (0.15+0.15+0.40+0.21).

In an exemplary embodiment, a process of manufacturing a nonwoven laminate includes forming an inner web comprised substantially of meltblown fibers, and bonding two or more outer webs comprised substantially of spunbond fibers to the inner web.

In an exemplary embodiment, the base fabric may be an "SMS" structure that may be produced with multiple beams of both spunbond and meltblown wherein the fabric has outer spunbond layers and inner meltblown layers of varying fiber distribution. According to an embodiment of the invention, the base fabric may be thermally pattern bonded.

In an exemplary embodiment, the base fabric may be an "SM" structure that may be produced with multiple beams of both spunbond and meltblown wherein the fabric has one outer spunbond layer and meltblown layers of varying fiber distribution. According to an embodiment of the invention, the base fabric may be thermally pattern bonded.

The SM structure can be layered into an SM-MS web structure, where the meltblown layers of two bonded webs are disposed adjacent to each other. The D-hump profile can be formed between any adjacent MB layers (for example, the MB barrier layer can be formed between NMN-NMN or NM-N or NBN-NB webs, etc.)

The following examples illustrate advantages of the present invention:

EXAMPLE 1

Trial #10 of FIG. 4A

A nonwoven having an SMS structure and a basis weight of 19 gsm (grams per square meter) was used. The sample included three meltblown (MB) sublayers with an MB basis weight of 3.6 gsm. Thus, the meltblown sublayers comprised 19% of the total weight of the nonwoven. The three MB sublayers formed a "hump" profile—a coarse MB sublayer between two fine MB sublayers—and exhibited a desirable LSTS average of 35 seconds (s) and a desirable AP of 29 $m^3/min/m^2$.

The three MB sublayers also formed a "D-hump" profile of NMN, with an increment coefficient difference of 1.8.

EXAMPLE 2

Trial #9 of FIG. 4A

This example demonstrated a retention of the desirable qualities obtained in Example 1 with a lower basis weight fabric. A nonwoven having an SMS structure and a basis weight of 17 gsm was used. The sample included three meltblown (MB) sublayers with an MB basis weight of 3.2 gsm. Thus, the meltblown sublayers also comprised 19% of the total weight of the nonwoven. The three MB sublayers formed a "hump" profile—a coarse MB sublayer between two fine MB sublayers—and exhibited a similarly desirable combination of a LSTS average of 29 s and an AP of 30 $m^3/min/m^2$.

The three MB sublayers also formed a "D-hump" profile of NMN, with an increment coefficient difference of 1.9.

EXAMPLE 3

Trial #28 of FIG. 4A

This example demonstrated similarly desirable qualities of a fabric formed with a slightly higher MB percentage from having an additional inner coarse MB sublayer. A nonwoven having an SMS structure and a basis weight of 19 gsm (grams per square meter) was used. The sample included four meltblown (MB) sublayers with an MB basis weight of 5.1 gsm. Thus, the meltblown sublayers also comprised 27% of the total weight of the nonwoven. The four MB sublayers formed a "hump" profile—two coarse MB sublayers between two fine MB sublayers—and exhibited a desirable LSTS average of 33 s and a desirable AP of 27 $m^3/min/m^2$.

The three MB sublayers also formed a flat fiber size distribution profile.

EXAMPLE 4

Trial #22 of FIG. 4A

This example also demonstrated desirable qualities of a fabric formed with a higher MB percentage from having an additional inner coarse MB sublayer. A nonwoven having an SMS structure and a basis weight of 19 gsm (grams per square meter) was used. The sample included four meltblown (MB) sublayers with an MB basis weight of 5.6 gsm. Thus, the meltblown sublayers also comprised 30% of the total weight of the nonwoven. The four MB sublayers formed a "hump" profile—two coarse MB sublayers between two fine MB sublayers—and exhibited a desirable LSTS average of 33 s and a desirable AP of 20 $m^3/min/m^2$.

The four MB sublayers also formed a "D-hump" profile of NMMN, with an increment coefficient difference of 2.3.

EXAMPLE 5

Trial #50 of FIG. 4B

A nonwoven having an SMS structure and a basis weight of 10 gsm (grams per square meter) was used. The sample included three meltblown (MB) sublayers with an MB basis weight of 1.4 gsm. Thus, the meltblown sublayers comprised 14% of the total weight of the nonwoven.

The three MB sublayers formed a "D-hump" profile (NMN with an increment coefficient difference of 1.7) and exhibited a desirable LSTS average of 10 seconds (s) and a desirable AP of 58 $m^3/min/m^2$.

EXAMPLE 6

Trial #51 of FIG. 4B

A nonwoven having an SM structure and a basis weight of 14 gsm (grams per square meter) was used. The sample included three meltblown (MB) sublayers with an MB basis weight of 6.3 gsm. Thus, the meltblown sublayers comprised 45% of the total weight of the nonwoven. The three MB sublayers formed a "D-hump" profile (NMN with an increment coefficient difference of 2.1) and exhibited a desirable LSTS average of 87 seconds (s) and a desirable AP of 27 $m^3/min/m^2$.

EXAMPLE 7

Trial #52 of FIG. 4B

A nonwoven having an SM structure and a basis weight of 14 gsm (grams per square meter) was used. The sample included three meltblown (MB) sublayers with an MB basis weight of 6.3 gsm. Thus, the meltblown sublayers comprised 45% of the total weight of the nonwoven. The three MB sublayers formed a "D-hump" profile (NMN with an increment coefficient difference of 2.1). Two such samples was put one on each other to create SM MS structure and exhibited a desirable LSTS average of more than 100 seconds (s) and a desirable AP of 13 $m^3/min/m^2$.

As previously discussed, to determine the fiber thickness distribution of a meltblown layer, at least 100 fiber thicknesses are measured in a sample. The results are set to 0.25 micrometre increments (forming a histogram). The fiber frequency within a given increment is recalculated into a percentage ratio. The increments can be shown in a plot (see FIG. 7).

In the case where one is knowledgeable of a production process configuration, it is possible to determine the potential layers by estimation and to verify this by measurement (e.g., during production of an SMS nonwoven textile on a production line with a beam configuration of S1M1M2M3 S2, small separators can be added between the production beams so that the MB layers can be separated and measured independently).

When examining an unknown sample, it is appropriate to perform, for example, utilising suitable technology and procedures, a cross-section of the nonwoven textile and in the first indicative measurement to determine whether the composition of the fibres corresponds to a layered textile structure and identify the location of the key layers in the structure, (e.g. in a cross-section of an unknown sample it is possible to compare 2 layers of spunbond fibres, the diameters of which are statistically distributed along the entire surfaces of the section and the layer of meltblown fibres, the diameters of which are distributed in such a way that adjacent to the SB fibres they are rather thicker fibres and in the middle of the layer rather thinner fibres. This leads to the hypothesis that the MB layer is in actual fact formed of three layers M1/M2/M3 with a hump or D-hump profile. This hypothesis may be verified by further measurement on separate MB layers.

To determine the fiber thickness distribution, a sample of nonwoven textile is taken from at least four locations at least 5 cm away from each other. In each sample, the diameter of at least 25 individual fibres for each observed layer is measured. It is possible to use, for example, an optical or scanning electron microscope (SEM) (depending on the diameter of the measured fibres) to measure fiber diameter. In the event that the diameter of fibers in one sample varies significantly from the other two, the entire sample is discarded and a new one is prepared. The measured values for each layer composed of all three samples are consolidated into a single set of values that are sorted to increments (with a 0.25 micron step).

Basis weight (g/m$^2$) is measured on a nonwoven textile using standardized testing methodology EN ISO 9073-1: 1989 (corresponding to norm WSP 130.1). For measurement, 10 layers of nonwoven textile are used, sample size is 10×10 cm$^2$. The basis weight of the individual layers is in the case where one is knowledgeable of production line configuration a known unit. In the event of an unknown sample, the basis weight of the layers can be approximately determined using various methods. A person skilled in the art is able to select a suitable methodology for specific cases.

For example, it is possible to mechanically separate the nonwoven textile layers from each other and then measure the basis weight as described above.

For example, the optical method can be used to determine in cross section the approximate borders of the individual layers and their fiber packing density. Together with the knowledge of the density of the polymer used, it is then possible to calculate an indicative basis weight of a layer.

Now that embodiments of the present invention have been shown and described in detail, various modifications and improvements thereon will become readily apparent to those skilled in the art. Accordingly, the spirit and scope of the present invention is to be construed broadly and not limited by the foregoing specification

The invention claimed is:

1. A nonwoven composite fabric comprising:
   a first nonwoven layer composed substantially of meltblown fibers, the fibers within the first nonwoven layer having diameters that vary in accordance with a first distribution;
   a second nonwoven layer composed substantially of meltblown fibers, the fibers within the second nonwoven layer having diameters that vary in accordance with a second distribution; and
   a third nonwoven layer composed substantially of meltblown fibers, the third nonwoven layer disposed between the first and second nonwoven layers, the fibers within the third nonwoven layer having diameters that vary in accordance with a third distribution that is greater than the first and second distributions.

2. The nonwoven composite fabric of claim 1, wherein the first and second nonwoven layers make up at least 30 weight % of the first, second and third nonwoven layers combined.

3. The nonwoven composite fabric of claim 1, wherein the first and second distributions are narrow or middle distributions,
   where narrow distribution indicates at least one increment of a sample of fibers forming a peak within the sample that has a frequency equal to or greater than 30% or indicates at least one increment of a sample of fibers forming a peak within the sample that has a frequency equal to or greater than 20% and no other peak over 5%, and
   where middle distribution indicates at least one increment of a sample of fibers forming a first peak within the sample that has a frequency equal to or greater than 20% and at least one other increment forming a second peak within the sample that has a frequency greater than 5%.

4. The nonwoven composite fabric of claim 3, wherein the third distribution is a middle or broad distribution,
   where broad distribution indicates that no increment of a sample of fibers forms a peak within the sample that has a frequency equal to or greater than 20%.

5. The nonwoven composite fabric of claim 4, wherein the first and second distributions are narrow distributions.

6. The nonwoven composite fabric of claim 5, wherein the third distribution is a middle distribution.

7. The nonwoven composite fabric of claim 5, wherein the third distribution is a broad distribution.

8. The nonwoven composite fabric of claim 4, wherein the first and second distributions are middle distributions.

9. The nonwoven composite fabric of claim 8, wherein the third distribution is a broad distribution.

10. The nonwoven composite fabric of claim 1, wherein an increment coefficient between the first distribution and the third distribution and between the second distribution and third distribution is at least 1.

11. The nonwoven composite fabric of claim 10, wherein the increment coefficient is at least 1.5.

12. The nonwoven composite fabric of claim 1, further comprising at least one layer composed substantially of spunbond fibers.

13. The nonwoven composite fabric of claim 1, wherein the first, second and third layers are disposed between at least two outer layers, the at least two outer layers composed substantially of spunbond fibers.

14. The nonwoven composite fabric of claim 13, wherein the nonwoven composite fabric has a basis weight of less than 10 gsm.

15. The nonwoven composite fabric of claim 13, wherein the nonwoven composite fabric has a Low Surface Tension Fluid Strikethrough Time of at least 25 seconds.

16. The nonwoven composite fabric of claim 13, wherein the nonwoven composite fabric has an air permeability of less than 50 $m^3/min/m^3$.

17. The nonwoven composite fabric of claim 1, wherein the fibers in the first and second nonwoven layers have an average fiber diameter that is less than an average fiber diameter of the fibers in the third nonwoven layer.

18. The nonwoven composite fabric of claim 1, wherein the fibers within the first, second and third nonwoven layers have an average diameter of less than 2 microns.

19. A nonwoven composite fabric comprising:
a first web comprising:
  a first nonwoven layer composed substantially of meltblown fibers, the fibers within the first nonwoven layer having diameters that vary in accordance with a first distribution;
  a second nonwoven layer composed substantially of meltblown fibers, the fibers within the second nonwoven layer having diameters that vary in accordance with a second distribution;
  a third nonwoven layer composed substantially of meltblown fibers, the third nonwoven layer disposed between the first and second nonwoven layers, the fibers within the third nonwoven layer having diameters that vary in accordance with a third distribution that is greater than the first and second distributions; and
  a fourth nonwoven layer composed substantially of spunbond fibers; and
a second web comprising:
  a fifth nonwoven layer composed substantially of meltblown fibers, the fibers within the fifth nonwoven layer having diameters that vary in accordance with a fifth distribution;
  a sixth nonwoven layer composed substantially of meltblown fibers, the fibers within the sixth nonwoven layer having diameters that vary in accordance with a sixth distribution; and
  a seventh nonwoven layer composed substantially of meltblown fibers, the seventh nonwoven layer disposed between the fifth and sixth nonwoven layers, the fibers within the seventh nonwoven layer having diameters that vary in accordance with a seventh distribution that is greater than the fifth and sixth distributions,
the first and second webs are disposed adjacent to one another so that the second nonwoven layer is directly facing with the sixth nonwoven layer.

20. The nonwoven composite fabric of claim 19, wherein the second web further comprises an eighth nonwoven layer composed substantially of spunbond fibers.

* * * * *